United States Patent
Yu et al.

(10) Patent No.: US 10,816,548 B2
(45) Date of Patent: *Oct. 27, 2020

(54) CELL LINE SCREENING METHOD

(71) Applicant: Larix Biosciences LLC, Sunnyvale, CA (US)

(72) Inventors: Bo Yu, Sunnyvale, CA (US); James Larrick, Sunnyvale, CA (US)

(73) Assignee: Larix Bioscience, LLC, Sunnyvale, CA (US)

( * ) Notice: Subject to any disclaimer, the term of this patent is extended or adjusted under 35 U.S.C. 154(b) by 143 days.

This patent is subject to a terminal disclaimer.

(21) Appl. No.: 15/899,051

(22) Filed: Feb. 19, 2018

(65) Prior Publication Data

US 2018/0313834 A1 Nov. 1, 2018

Related U.S. Application Data

(63) Continuation of application No. 14/092,786, filed on Nov. 27, 2013, now Pat. No. 9,910,038.

(60) Provisional application No. 61/732,156, filed on Nov. 30, 2012.

(51) Int. Cl.
| | |
|---|---|
| *C12N 15/63* | (2006.01) |
| *C12Q 1/6897* | (2018.01) |
| *G01N 33/569* | (2006.01) |
| *C07K 16/00* | (2006.01) |
| *C12N 15/10* | (2006.01) |
| *C07K 16/28* | (2006.01) |

(52) U.S. Cl.
CPC ....... *G01N 33/56966* (2013.01); *C07K 16/00* (2013.01); *C07K 16/2887* (2013.01); *C12N 15/1086* (2013.01); *C12N 15/63* (2013.01); *C12Q 1/6897* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 6,406,863 B1 | 6/2002 | Zhu et al. | |
| 7,732,195 B2 | 6/2010 | Akamatsu et al. | |
| 7,947,495 B2 | 5/2011 | DuBridge et al. | |
| 8,163,546 B2 | 4/2012 | Akamatsu et al. | |
| 9,910,038 B2 * | 3/2018 | Yu ................... | G01N 33/56966 |
| 2004/0219611 A1 | 11/2004 | Racher | |
| 2007/0111260 A1 | 5/2007 | Gao et al. | |
| 2010/0291626 A1 | 11/2010 | Chen et al. | |
| 2011/0008883 A1 | 1/2011 | Akamatsu et al. | |
| 2013/0071881 A1 | 3/2013 | Ohmori et al. | |

FOREIGN PATENT DOCUMENTS

| | | |
|---|---|---|
| CN | 102762728 | 10/2012 |
| EP | 1 293 564 | 3/2003 |
| JP | 2011826645 | 9/2011 |
| WO | WO 2003/070931 | 8/2003 |
| WO | WO 2004/007686 | 1/2004 |
| WO | WO 2004/029284 | 4/2004 |
| WO | WO 2010/022961 | 3/2010 |

OTHER PUBLICATIONS

Kito et al., Construction of engineered CHO strains for high level production of recombinant proteins, 2002, Appl Microbiol Biotech vol. 60, pp. 442-448.
Suehiro et al., Transient and permanent gene transfer into the brain of the teleost fish medaka, 2010, FEBS Lett vol. 584, pp. 3545-3549.
Awasthi et al., Analysis of splice variants of the immediate early 1 region of human cytomegalovirus, 2004, J. Virol. vol. 78, pp. 8191-8200.
Baek et al., Construction of a large synthetic human Fab antibody library on yeast cell surface by optimized yeast mating, 2014, J. Microbiol. Biotechnol. vol. 24, pp. 408-420.
Benson et al., Heterogeneous nuclear ribonucleoprotein L-like (hnRNPLL) and elongation factor . . . plasma cells, Oct. 2012, Proc Natl Acad Sci vol. 109, 16252-257.
Beuzelin et al., Structure-function relationships of the variable domains of monoclonal antibodies . . . treatment, 2007, Crit Rev Oncol Hematol vol. 64, pp. 210-225.
Bowers et al., Coupling mammalian cell surface display with somatic hypermutation . . . human antibodies, 2011, Proc Natl Acad Sci vol. 108, pp. 20455-460.
Brezinsky, et al., A simple method for enriching populations of transfected CHO cells for cells . . . productivity, 2003, J. Immunol. Meth. vol. 277, pp. 141-155.
Coronella et al., Amplification of IgG VH and VL (Fab) from single human plasma cells and B cells, 2000, Nucl. Acids Res. vol. 28, p. e85.
Demaria et al., Accelerated clone selection for recombinant CHO cells using a FACS . . . screen, 2007, Biotechnol Prog vol. 23, pp. 465-472.
Demaria, Utilization of non-AUG initiation codons in a FACs method for rapid selection of recombinant cell lines, Feb. 2012, Cell Culture World Congress.
Dove, Antibody production branches out, 2009, Nature Meth. vol. 6, pp. 851-855.
Dunnick et al., DNA sequences at immunoglobulin switch region recombination sites, 1993, Nucl. Acids Res. vol. 21, pp. 365-372.
Edwards-Gilbert et al., Alternative poly(A) site selection in complex transcirption units: means to an end? 1997, Nucl. Acids Res. vol. 25, pp. 2547-2561.

(Continued)

Primary Examiner — Channing S Mahatan
(74) Attorney, Agent, or Firm — HelixIP LLP

(57) ABSTRACT

The invention provides a novel cell line development method useful to screen for recombinant protein production. The method utilizes a membrane-anchored reporter or an intracellular reporter residing in the expression vector for a gene of interest to facilitate initial cell selection by FACS or MACS. A switching mechanism can be used to delete the reporter from the chromosome by providing an appropriate DNA recombinase, which turns the selected cells into production cells that secrete the protein of interest without co-expression of the reporter.

20 Claims, 15 Drawing Sheets

Specification includes a Sequence Listing.

(56) References Cited

OTHER PUBLICATIONS

Firer et al., Targeted drug delivery for cancer therapy: the other side of antibodies, Nov. 2012, J. Hematol. Oncol. vol. 5, p. 70.
Han et al., Overlapping activation-induced cytidine deaminase hotspot motifs in IG class-switch recombination, 2011, Proc Natl Acad Sci vol. 108, pp. 11584-11589.
Ho et al., Isolation of anti-CD22 Fv with high affinity by Fv display on human cells, 2006, Proc. Natl Acad. Sci. vol. 103, pp. 9637-9642.
Hoogenboom, Selecting and screening recombinant antibody libraries, 2005, Nature Biotechnol. vol. 23, pp. 1105-1116.
Horlick et al., Simultaneous surface display and secretion of proteins from mammalian cells . . . antibodies, May 2013, J. Biol. Chem. vol. 288, pp. 19861-19869.
Jones et al., Advances in the development of therapeutic monoclonal antibodies, 2007, BioPharm. Intl vol. 20, pp. 96-114.
Jose et al., The autodisplay story, from discovery to biotechnical and biomedical application, 2007, Microbiol. Molc. Biol. Rev. vol. 71, pp. 600-619.
Kaufman et al., Homogeneity and persistence of transgene expression by omitting antibiotic . . . line isolation, 2008, Nucl. Acids Res. vol. 36, p. e111.
Kim et al., Antibody engineering for the development of therapeutic antibodies, 2005, Mol. Cells vol. 20, pp. 17-29.
Knight et al., Antigen endocytosis and presentation mediated by human membrane IgG1 . . . Igalpha/Igbeta dimer, 1997, EMBO J. vol. 16, pp. 3842-3850.
Kurosawa et al., Rapid production of antigen-specific monocolonal antibodies from a variety of animals, Sep. 2012, BMC Biol. vol. 10, p. 80.
Kwakkenbos et al., Generation of stable monoclonal antibody-producing BCR human memory B cells . . . programming, 2010, Nat Med vol. 16, pp. 123-128.
Li et al., Cell culture processes for monoclonal antibody production, 2010, mAbs vol. 2, pp. 466-477.
Lin et al., B-cell display-based one-step method to generate chimeric human IgG monoclonal antibodies, 2010, Nucl. Acids Res. vol. 39, p. e14.
McConnell et al., High affinity humanized antibodies without making hybridomas . . . somatic hypermutation, Nov. 2012, PLoS One vol. 7, p. e49458.
Munro et al., Bridging the gap, facilities and technologies for development of early stage . . . candidates, 2011, mAbs vol. 3, pp. 440-452.
Ni, New technologies for the generation of human monoclonal antibody, 2009, Trends Biopharm Ind vol. 5, pp. 3-12.
Ozawa et al., Amplification and analysis of cDNA generated from a single cell by 5'-RACE . . . single B cells, 2006, Biotechniq. vol. 40, pp. 469-478.
Peine, Production of mammalian glycoproteins for structural analysis: site-specific recombination . . . CHO cells, 2011, Thesis.
Pepper et al., A decade of yeast surface display technology: where are we now? 2008, Comb Chem High Throughput Screen vol. 11, pp. 127-134.
Pilbrough et al., Intraclonal protein expression heterogeneity in recombinant CHO cells, 2009, PLoS One vol. 4, p. e8432.
Shapiro et al., RNA splice junctions of different classes of eukaryotes: sequence statistics . . . gene expression, 1987, Nucl. Acids Res. vol. 15, pp. 7155-7174.
Tiller et al., Cloning and expression of murine Ig genes from single B cells, 2009, J. Immunol. Meth. vol. 350, pp. 183-193.
Wang et al., Advances in the production of human monoclonal antibodies, 2011, Antibody Technol. J. vol. 1, pp. 1-4.
Wilke et al., Glycoprotein production for structure analysis with stable, glycosylation mutant . . . cell sorting, 2010, Prot. Sci. vol. 19, pp. 1264-1271.
Wilke et al., Streamlining homogeneous glycoprotein production for biophysical . . . cell line development, 2011, PLoS One vol. 6, p. e27829.
Wine et al., Molecular deconvolution of the monoclonal antibodies that comprise the polyclonal serum response, Feb. 2013, Proc Natl Acad Sci vol. 110, pp. 2993-2998.
Yoshimoto et al., High-throughput de novo screening of receptor agonists with an automated . . . isolation system, Feb. 2014, Scientific Rep vol. 4, p. 4242.
Zhou et al., Development of a novel mammalian cell surface antibody display platform, 2010, mAbs vol. 2, pp. 508-518.
Zhou et al., Four-way ligation for construction of a mammalian cell-based full-length antibody display library, 2011, Acta Biochim Biophys vol. 43, pp. 232-238.
Kapusi et al., PhiC31 intergrase mediated site specific recombination in Barley, Sep. 2012, PLoS One vol. 7, p. e45353.
Meuwissen et al., Mouse model for lung tumorigenesis through Cre/lox sporadic . . . K-ras oncogene, 2001, Oncogene, Sci & Med Div, MacMillan Press, vol. 20, pp. 6551-6558.
Li et al., Construction and development of a mammalian cell-based full length antibody library for targeting . . . , Jul. 2012, Appl Microbiol Biotech vol. 96, pp. 1233-1241.

\* cited by examiner

Membrane-anchored POI

Secreted POI

Membrane-anchored POI
(Exon 2 deleted)

Secreted POI

SEQUENCE LISTING

```
<160> NUMBER OF SEQ ID NOS: 23

<210> SEQ ID NO 1
<211> LENGTH: 906
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgtacagga tgcaactcct gtcttgcatt gcactaagtc ttgcacttgt cacgaattcg     60
gtgagcaagg gcgaggagct gttcaccggg gtggtgccca tcctggtcga gctggacggc    120
gacgtaaacg gccacaagtt cagcgtgtcc ggcgagggcg agggcgatgc cacctacggc    180
aagctgaccc tgaagttcat ctgcaccacc ggcaagctgc ccgtgccctg gcccaccctc    240
gtgaccaccc tgacctacgg cgtgcagtgc ttcagccgct accccgacca catgaagcag    300
cacgacttct tcaagtccgc catgcccgaa ggctacgtcc aggagcgcac catcttcttc    360
aaggacgacg gcaactacaa gacccgcgcc gaggtgaagt tcgagggcga caccctggtg    420
aaccgcatcg agctgaaggg catcgacttc aaggaggacg gcaacatcct ggggcacaag    480
ctggagtaca actacaacag ccacaacgtc tatatcatgg ccgacaagca gaagaacggc    540
atcaaggtga acttcaagat ccgccacaac atcgaggacg gcagcgtgca gctcgccgac    600
cactaccagc agaacacccc catcggcgac ggccccgtgc tgctgcccga caaccactac    660
ctgagcaccc agtccgccct gagcaaagac cccaacgaga gcgcgatca catggtcctg    720 ctggagttcg tgaccgccgc cgggatcact ctcggcatgg acgagctgta caagtccgga    780
```

-continued

```
catgaaacaa ccccaaataa aggaagtgga accacttcag gtactacccg tcttctatct    840
gggcacacgt gtttcacgtt gacaggtttg cttgggacgc tagtaaccat gggcttgctg    900
acttag                                                                906
```

<210> SEQ ID NO 2
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Tyr Arg Met Gln Leu Leu Ser Cys Ile Ala Leu Ser Leu Ala Leu
1               5                   10                  15

Val Thr Asn Ser Val Ser Lys Gly Glu Glu Leu Phe Thr Gly Val Val
                20                  25                  30

Pro Ile Leu Val Glu Leu Asp Gly Asp Val Asn Gly His Lys Phe Ser
            35                  40                  45

Val Ser Gly Glu Gly Glu Gly Asp Ala Thr Tyr Gly Lys Leu Thr Leu
        50                  55                  60

Lys Phe Ile Cys Thr Thr Gly Lys Leu Pro Val Pro Trp Pro Thr Leu
65                  70                  75                  80

Val Thr Thr Leu Thr Tyr Gly Val Gln Cys Phe Ser Arg Tyr Pro Asp
                85                  90                  95

His Met Lys Gln His Asp Phe Phe Lys Ser Ala Met Pro Glu Gly Tyr
            100                 105                 110

Val Gln Glu Arg Thr Ile Phe Phe Lys Asp Asp Gly Asn Tyr Lys Thr
        115                 120                 125

Arg Ala Glu Val Lys Phe Glu Gly Asp Thr Leu Val Asn Arg Ile Glu
    130                 135                 140

Leu Lys Gly Ile Asp Phe Lys Glu Asp Gly Asn Ile Leu Gly His Lys
145                 150                 155                 160

Leu Glu Tyr Asn Tyr Asn Ser His Asn Val Tyr Ile Met Ala Asp Lys
                165                 170                 175

Gln Lys Asn Gly Ile Lys Val Asn Phe Lys Ile Arg His Asn Ile Glu
            180                 185                 190

Asp Gly Ser Val Gln Leu Ala Asp His Tyr Gln Gln Asn Thr Pro Ile
        195                 200                 205

Gly Asp Gly Pro Val Leu Leu Pro Asp Asn His Tyr Leu Ser Thr Gln
    210                 215                 220

Ser Ala Leu Ser Lys Asp Pro Asn Glu Lys Arg Asp His Met Val Leu
225                 230                 235                 240

Leu Glu Phe Val Thr Ala Ala Gly Ile Thr Leu Gly Met Asp Glu Leu
                245                 250                 255

Tyr Lys Ser Gly His Glu Thr Thr Pro Asn Lys Gly Ser Gly Thr Thr
            260                 265                 270

Ser Gly Thr Thr Arg Leu Leu Ser Gly His Thr Cys Phe Thr Leu Thr
        275                 280                 285

Gly Leu Leu Gly Thr Leu Val Thr Met Gly Leu Leu Thr
    290                 295                 300
```

<210> SEQ ID NO 3
<211> LENGTH: 1596
<212> TYPE: DNA
<213> ORGANISM: Homo sapiens

<400> SEQUENCE: 3

```
agcaccaagg gcccatcggt cttcccctg gcaccctcct ccaagagcac ctctgggggc      60
acagcggccc tgggctgcct ggtcaaggac tacttcccg aaccggtgac ggtgtcgtgg     120
aactcaggcg ccctgaccag cggcgtgcac accttcccgg ctgtcctaca gtcctcagga    180
ctctactccc tcagcagcgt ggtgaccgtg ccctccagca gcttgggcac ccagacctac    240
atctgcaacg tgaatcacaa gcccagcaac accaaggtgg acaagaaagt tggtgagagg    300
ccagcacagg gagggagggt gtctgctgga agccaggctc agcgctcctg cctggacgca    360
tcccggctat gcagcccag tccagggcag caaggcaggc ccgtctgcc tcttcacccg     420
gaggcctctg cccgcccac tcatgctcag ggagagggtc ttctggcttt tccccaggc     480
tctgggcagg cacaggctag gtgcccctaa cccaggccct gcacacaaag ggcaggtgc     540
tgggctcaga cctgccaaga gccatatccg ggaggaccct gcccctgacc taagcccacc    600
ccaaaggcca aactctccac tccctcagct cggacacctt ctctcctccc agattccagt    660
aactcccaat cttctctctg cagagcccaa atcttgtgac aaaactcaca catgcccacc    720
gtgcccaggt aagccagccc aggcctcgcc ctccagctca aggcgggaca ggtgccctag    780
agtagcctgc atccagggac aggccccagc cgggtgctga cacgtccacc tccatctctt    840
cctcagcacc tgaactcctg gggggaccgt cagtcttcct cttccccca aaacccaagg    900
acaccctcat gatctcccgg acccctgagg tcacatgcgt ggtggtggac gtgagccacg    960
aagaccctga ggtcaagttc aactggtacg tggacggcgt ggaggtgcat aatgccaaga   1020
caaagccgcg ggaggagcag tacaacagca cgtaccgtgt ggtcagcgtc ctcaccgtcc   1080
tgcaccagga ctggctgaat ggcaaggagt acaagtgcaa ggtctccaac aaagccctcc   1140
cagcccccat cgagaaaacc atctccaaag ccaaaggtgg acccgtgggg gtgcgagggc   1200
cacatggaca gaggccggct cggcccaccc tctgccctga gagtgaccgc tgtaccaacc   1260
tctgtcccta caggcagcc ccgagaacca caggtgtaca ccctgccccc atcccgggat   1320
gagctgacca agaaccaggt cagcctgacc tgcctggtca aaggcttcta tcccagcgac   1380
atcgccgtgg agtgggagag caatgggcag ccggagaaca actacaagac cacgcctccc   1440
gtgctggact ccgacggctc cttcttcctc tacagcaagc tcaccgtgga caagagcagg   1500
tggcagcagg ggaacgtctt ctcatgctcc gtgatgcatg aggctctgca caaccactac   1560
acgcagaaga gcctctcct gtctccgggt aaatga                              1596
```

<210> SEQ ID NO 4
<211> LENGTH: 123
<212> TYPE: DNA
<213> ORGANISM: Homo sapiens

<400> SEQUENCE: 4

```
catgaaacaa cccaaataa aggaagtgga accacttcag gtactacccg tcttctatct      60
gggcacacgt gtttcacgtt gacaggtttg cttgggacgc tagtaaccat gggcttgctg    120
act                                                                  123
```

<210> SEQ ID NO 5
<211> LENGTH: 41
<212> TYPE: PRT
<213> ORGANISM: Homo sapiens

<400> SEQUENCE: 5

His Glu Thr Thr Pro Asn Lys Gly Ser Gly Thr Thr Ser Gly Thr Thr
1               5                   10                  15

Arg Leu Leu Ser Gly His Thr Cys Phe Thr Leu Thr Gly Leu Leu Gly
            20                  25                  30

Thr Leu Val Thr Met Gly Leu Leu Thr
        35                  40

<210> SEQ ID NO 6
<211> LENGTH: 147
<212> TYPE: DNA
<213> ORGANISM: Unknown
<220> FEATURE:
<223> OTHER INFORMATION: Description of Unknown: Platelet derived growth
      factor receptor transmembrane domain polynucleotide

<400> SEQUENCE: 6
gctgtgggcc aggacacgca ggaggtcatc gtggtgccac actccttgcc ctttaaggtg    60
gtggtgatct cagccatcct ggccctggtg gtgctcacca tcatctccct tatcatcctc   120
atcatgcttt ggcagaagaa gccacgt                                      147

<210> SEQ ID NO 7
<211> LENGTH: 49
<212> TYPE: PRT
<213> ORGANISM: Unknown
<220> FEATURE:
<223> OTHER INFORMATION: Description of Unknown: Platelet derived growth
      factor receptor transmembrane domain polypeptide

<400> SEQUENCE: 7

Ala Val Gly Gln Asp Thr Gln Glu Val Ile Val Val Pro His Ser Leu
1               5                   10                  15

Pro Phe Lys Val Val Val Ile Ser Ala Ile Leu Ala Leu Val Val Leu
            20                  25                  30

Thr Ile Ile Ser Leu Ile Ile Leu Ile Met Leu Trp Gln Lys Lys Pro
        35                  40                  45

Arg

<210> SEQ ID NO 8
<211> LENGTH: 34
<212> TYPE: DNA
<213> ORGANISM: Unknown
<220> FEATURE:
<223> OTHER INFORMATION: Description of Unknown: LoxP
      oligonucleotide

<400> SEQUENCE: 8
ataacttcgt atagcataca ttatacgaag ttat                              34

<210> SEQ ID NO 9
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgtatctgg gattgaattg cgtcattatc gtgtttctgc tcaagggtgt gcaaagtcag    60
gtccagctgc agcagccagg cgcagagctg gttaagccag agcctcagt gaaaatgagc   120 tgcaaagcct ctggctacac ctttaccagc tataacatgc attgggtgaa acagacaccc   180
ggcagagggc tggaatggat cggagccata taccccggga acggggacac ctcctataac   240

```
cagaagttca agggaaaggc cacactcact gctgacaagt ccagtagcac cgcttacatg    300
caactttcaa gcttgacatc agaggattct gcagtttact actgtgcccg gtctacttac    360
tatggcggcg attggtattt caatgtatgg ggtgctggca acagtcac tgtgagcgca      420 gct                                                                  423
```

<210> SEQ ID NO 10
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Tyr Leu Gly Leu Asn Cys Val Ile Ile Val Phe Leu Leu Lys Gly
1               5                  10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Gly Gly Asp Trp Tyr Phe Asn
        115                 120                 125

Val Trp Gly Ala Gly Thr Thr Val Thr Val Ser Ala Ala
    130                 135                 140
```

<210> SEQ ID NO 11
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgaaactcc cagtcaggct gctggtgctt atgttctgga tacccgccag ttcatctcag     60
attgtcttga ccagtctcc cgccatttg tctgcctccc ctggggagaa agtaaccatg      120
acttgtcgcg catcctcaag cgtgagttac atccactggt tcagcagaa gcctggcagc     180 tcacccaagc cctggatcta tgctacctcc aacctcgctt ccggagtgcc tgtgcggttt    240
tctgggtccg gtagtggtac cagctactca ctgactattt caagagttga ggctgaagat    300
gccgcaacct attactgcca acagtggaca gtaatccac caacattcgg tggcggcact    360
aaactggaga tcaaacgtac ggtggctgca ccatctgtct tcatcttccc gccatctgat    420
gagcagttga atctggaac tgcctctgtt gtgtgcctgc tgaataactt ctatcccaga    480
gaggccaaag tacagtggaa ggtggataac gccctccaat cgggtaactc ccaggagagt    540
gtcacagagc aggacagcaa ggacagcacc tacagcctca gcagcaccct gacgctgagc    600
aaagcagact acgagaaaca caaagtctac gcctgcgaag tcacccatca gggcctgagc    660
```
tcgcccgtca caaagagctt caacagggga gagtgt 696

```
<210> SEQ ID NO 12
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 12

```
Met Lys Leu Pro Val Arg Leu Leu Val Leu Met Phe Trp Ile Pro Ala
1               5                   10                  15

Ser Ser Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

```
<210> SEQ ID NO 13
<211> LENGTH: 1631
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 13
agcaccaagg gcccatcggt cttccccctg gcaccctcct ccaagagcac ctctgggggc 60
acagcggccc tgggctgcct ggtcaaggac tacttccccg aaccggtgac ggtgtcgtgg 120
aactcaggcg ccctgaccag cggcgtgcac accttcccgg ctgtcctaca gtcctcagga 180
ctctactccc tcagcagcgt ggtgaccgtg ccctccagca gcttgggcac ccagacctac 240
atctgcaacg tgaatcacaa gcccagcaac accaaggtgg acaagaaagt tggtgagagg 300

```
ccagcacagg gagggagggt gtctgctgga agccaggctc agcgctcctg cctggacgca      360
tcccggctat gcagcccag tccagggcag caaggcaggc cccgtctgcc tcttcacccg       420
gaggcctctg cccgcccac tcatgctcag ggagagggtc ttctggcttt tcccccaggc       480
tctgggcagg cacaggctag gtgcccctaa cccaggccct gcacacaaag gggcaggtgc      540
tgggctcaga cctgccaaga gccatatccg ggaggaccct gcccctgacc taagcccacc     600
ccaaaggcca aactctccac tccctcagct cggacacctt ctctcctccc agattccagt     660
aactcccaat cttctctctg cagagcccaa atcttgtgac aaaactcaca catgcccacc    720
gtgcccaggt aagccagccc aggcctcgcc ctccagctca aggcgggaca ggtgccctag    780
agtagcctgc atccagggac aggccccagc cgggtgctga cacgtccacc tccatctctt   840
cctcagcacc tgaactcctg gggggaccgt cagtcttcct cttcccccca aaacccaagg    900
acaccctcat gatctcccgg acccctgagg tcacatgcgt ggtggtggac gtgagccacg    960
aagaccctga ggtcaagttc aactggtacg tggacggcgt ggaggtgcat aatgccaaga   1020
caaagccgcg ggaggagcag tacaacagca cgtaccgtgt ggtcagcgtc ctcaccgtcc   1080
tgcaccagga ctggctgaat ggcaaggagt acaagtgcaa ggtctccaac aaagccctcc   1140
cagcccccat cgagaaaacc atctccaaag ccaaaggtgg acccgtgggg tgcgagggc    1200 cacatggaca gaggccggct cggccccata acttcgtata gcatacatta tacgaagtta   1260
taccctctgc cctgagagtg accgctgtac caacctctgt ccctacaggg cagccccgag   1320
aaccacaggt gtacaccctg cccccatccc gggatgagct gaccaagaac caggtcagcc   1380
tgacctgcct ggtcaaaggc ttctatccca gcgacatcgc cgtggagtgg gagagcaatg   1440
ggcagccgga gaacaactac aagaccacgc ctcccgtgct ggactccgac ggctccttct   1500
tcctctacag caagctcacc gtggacaaga gcaggtggca gcagggaac gtcttctcat    1560 gctccgtgat gcatgaggct ctgcacaacc actacacgca agagcctc tccctgtctc      1620 cgggtaaatg a                                                         1631

<210> SEQ ID NO 14
<211> LENGTH: 2170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
agcaccaagg gcccatcggt cttccccctg gcaccctcct ccaagagcac ctctgggggc     60
acagcggccc tgggctgcct ggtcaaggac tacttccccg aaccggtgac ggtgtcgtgg    120
aactcaggcg ccctgaccag cggcgtgcac accttcccgg ctgtcctaca gtcctcagga   180
ctctactccc tcagcagcgt ggtgaccgtg ccctccagca gcttgggcac ccagacctac   240
atctgcaacg tgaatcacaa gcccagcaac accaaggtgg acaagaaagt tggtgagagg   300
ccagcacagg gagggagggt gtctgctgga agccaggctc agcgctcctg cctggacgca    360
tcccggctat gcagcccag tccagggcag caaggcaggc cccgtctgcc tcttcacccg    420
gaggcctctg cccgcccac tcatgctcag ggagagggtc ttctggcttt tcccccaggc    480
tctgggcagg cacaggctag gtgcccctaa cccaggccct gcacacaaag gggcaggtgc   540
tgggctcaga cctgccaaga gccatatccg ggaggaccct gcccctgacc taagcccacc   600
ccaaaggcca aactctccac tccctcagct cggacacctt ctctcctccc agattccagt   660
```

```
aactcccaat cttctctctg cagagcccaa atcttgtgac aaaactcaca catgcccacc    720
gtgcccaggt aagccagccc aggcctcgcc ctccagctca aggcgggaca ggtgccctag    780
agtagcctgc atccagggac aggccccagc cgggtgctga cacgtccacc tccatctctt    840
cctcagcacc tgaactcctg gggggaccgt cagtcttcct cttcccccca aaacccaagg    900
acaccctcat gatctcccgg acccctgagg tcacatgcgt ggtggtggac gtgagccacg    960
aagaccctga ggtcaagttc aactggtacg tggacggcgt ggaggtgcat aatgccaaga   1020
caaagccgcg ggaggagcag tacaacagca cgtaccgtgt ggtcagcgtc ctcaccgtcc   1080
tgcaccagga ctggctgaat ggcaaggagt acaagtgcaa ggtctccaac aaagccctcc   1140 cagccccat cgagaaaacc atctccaaag ccaaggtgg acccgtggg gtgcgagggc   1200 cacatggaca gaggccggct cggccccata acttcgtata gcatacatta tacgaagtta   1260
taccctctgc cctgagagtg accgctgtac caacctctgt ccctacaggg cagccccgag   1320
aaccacaggt gtacaccctg cccccatccc gggatgagct gaccaagaac caggtcagcc   1380
tgacctgcct ggtcaaaggc ttctatccca gcgacatcgc cgtggagtgg gagagcaatg   1440
ggcagccgga gaacaactac aagaccacgc ctcccgtgct ggactccgac ggctccttct   1500
tcctctacag caagctcacc gtggacaaga gcaggtggca gcagggaaac gtcttctcat   1560
gctccgtgat gcatgaggct ctgcacaacc actacacgca gaagagcctc tccctgtctc   1620
cgggtaaatc cggacatgaa caaccccaa ataaggaag tgaaccact tcaggtacta   1680 cccgtcttct atctgggcac acgtgtttca cgttgacagg tttgcttggg acgctagtaa   1740
ccatgggctt gctgacttaa actagtataa cttcgtatag catacattat acgaagttat   1800
accctctgcc ctgagagtga ccgctgtacc aacctctgtc cctacagggc agccccgaga   1860
accacaggtg tacaccctgc ccccatcccg ggatgagctg accaagaacc aggtcagcct   1920
gacctgcctg gtcaaaggct tctatcccag cgacatcgcc gtggagtggg agagcaatgg   1980
gcagccggag aacaactaca agaccacgcc tcccgtgctg gactccgacg gctccttctt   2040
cctctacagc aagctcaccg tggacaagag caggtggcag caggggaacg tcttctcatg   2100
ctccgtgatg catgaggctc tgcacaacca ctacacgcag aagagcctct ccctgtctcc   2160
gggtaaatga                                                          2170
```

<210> SEQ ID NO 15
<211> LENGTH: 2194
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
agcaccaagg gcccatcggt cttccccctg gcaccctcct ccaagagcac ctctgggggc     60
acagcggccc tgggctgcct ggtcaaggac tacttccccg aaccggtgac ggtgtcgtgg    120
aactcaggcg ccctgaccag cggcgtgcac accttcccgg ctgtcctaca gtcctcagga    180
ctctactccc tcagcagcgt ggtgaccgtg ccctccagca gcttgggcac ccagacctac    240
atctgcaacg tgaatcacaa gcccagcaac accaaggtgg acaagaaagt tggtgagagg    300
ccagcacagg gagggagggt gtctgctgga agccaggctc agcgctcctg cctggacgca    360
tcccggctat gcagccccag tcagggcag caaggcaggc cccgtctgcc tcttcacccg    420
gaggcctctg cccgccccac tcatgctcag ggagagggtc ttctggcttt ttccccaggc    480
```

```
tctgggcagg cacaggctag gtgcccctaa cccaggccct gcacacaaag gggcaggtgc      540
tgggctcaga cctgccaaga gccatatccg ggaggaccct gcccctgacc taagcccacc      600
ccaaaggcca aactctccac tccctcagct cggacacctt ctctcctccc agattccagt      660
aactcccaat cttctctctg cagagcccaa atcttgtgac aaaactcaca catgcccacc      720
gtgcccaggt aagccagccc aggcctcgcc ctccagctca aggcgggaca ggtgccctag      780
agtagcctgc atccagggac aggccccagc cgggtgctga cacgtccacc tccatctctt      840
cctcagcacc tgaactcctg gggggaccgt cagtcttcct cttcccccca aacccaagg       900 acaccctcat gatctcccgg acccctgagg tcacatgcgt ggtggtggac gtgagccacg      960
aagaccctga ggtcaagttc aactggtacg tggacggcgt ggaggtgcat aatgccaaga    1020
caaagccgcg ggaggagcag tacaacagca cgtaccgtgt ggtcagcgtc ctcaccgtcc    1080
tgcaccagga ctggctgaat ggcaaggagt acaagtgcaa ggtctccaac aaagccctcc    1140
cagcccccat cgagaaaacc atctccaaag ccaaaggtgg gacccgtggg gtgcgagggc    1200
cacatggaca gaggccggct cggccccata acttcgtata gcatacatta tacgaagtta    1260
taccctctgc cctgagagtg accgctgtac caacctctgt ccctacaggg cagccccgag    1320
aaccacaggt gtacaccctg cccccatccc gggatgagct gaccaagaac caggtcagcc    1380
tgacctgcct ggtcaaaggc ttctatccca gcgacatcgc cgtggagtgg gagagcaatg    1440
ggcagccgga gaacaactac aagaccacgc ctcccgtgct ggactccgac ggctccttct    1500
tcctctacag caagctcacc gtggacaaga gcaggtggca gcaggggaac gtcttctcat    1560
gctccgtgat gcatgaggct ctgcacaacc actacacgca gaagagcctc tccctgtctc    1620
cgggtaaatc cggagctgtg gccaggaca cgcaggagg catcgtggtg ccacactcct      1680 tgcccttta ggtggtggtg atctcagcca tcctggccct ggtggtgctc accatcatct     1740
cccttatcat cctcatcatg ctttggcaga agaagccacg ttaaactagt ataacttcgt   1800
atagcataca ttatacgaag ttataccctc tgccctgaga gtgaccgctg taccaacctc   1860
tgtccctaca gggcagcccc gagaaccaca ggtgtacacc ctgccccat cccgggatga    1920 gctgaccaag aaccaggtca gcctgacctg cctggtcaaa ggcttctatc ccagcgacat   1980
cgccgtggag tgggagagca tgggcagcc ggagaacaac tacaagacca cgcctcccgt    2040
gctggactcc gacggctcct tcttcctcta cagcaagctc accgtggaca agagcaggtg    2100
gcagcagggg aacgtcttct catgctccgt gatgcatgag gctctgcaca accactacac    2160
gcagaagagc ctctccctgt ctccgggtaa atga                                2194
```

<210> SEQ ID NO 16
<211> LENGTH: 1876
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
agcaccaagg gcccatcggt cttccccctg gcaccctcct ccaagagcac ctctgggggc       60
acagcggccc tgggctgcct ggtcaaggac tacttccccg aaccggtgac ggtgtcgtgg      120
aactcaggcg ccctgaccag cggcgtgcac accttcccgg ctgtcctaca gtcctcagga      180
ctctactccc tcagcagcgt ggtgaccgtg ccctccagca gcttgggcac ccagacctac      240
atctgcaacg tgaatcacaa gcccagcaac accaaggtgg acaagaaagt tggtgagagg      300
```

```
ccagcacagg gagggagggt gtctgctgga agccaggctc agcgctcctg cctggacgca    360
tcccggctat gcagcccag tccagggcag caaggcaggc ccgtctgcc tcttcacccg      420 gaggcctctg cccgccccac tcatgctcag ggagagggtc ttctggcttt tcccccaggc    480
tctgggcagg cacaggctag gtgcccctaa cccaggccct gcacacaaag ggcaggtgc     540 tgggctcaga cctgccaaga gccatatccg ggaggaccct gcccctgacc taagcccacc    600
ccaaaggcca aactctccac tccctcagct cggacaccct tctcctcccc agattccagt    660
aactcccaat cttctctctg cagagcccaa atcttgtgac aaaactcaca catgcccacc    720
gtgcccaggt aagccagccc aggcctcgcc ctccagctca aggcgggaca ggtgccctag    780
agtagcctgc atccagggac aggccccagc cgggtgctga cacgtccacc tccatctctt    840
cctcagcacc tgaactcctg gggggaccgt cagtcttcct cttccccca aaacccaagg     900 acaccctcat gatctcccgg acccctgagg tcacatgcgt ggtggtggac gtgagccacg    960
aagaccctga ggtcaagttc aactggtacg tggacggcgt ggaggtgcat aatgccaaga    1020
caaagccgcg ggaggagcag tacaacagca cgtaccgtgt ggtcagcgtc ctcaccgtcc    1080
tgcaccagga ctggctgaat ggcaaggagt acaagtgcaa ggtctccaac aaagccctcc    1140
cagcccccat cgagaaaacc atctccaaag ccaaaggtgg acccgtgggg tgcgagggc    1200 cacatggaca gaggccggct cggccccata acttcgtata gcatacatta tacgaagtta    1260
taccctctgc cctgagagtg accgctgtac caacctctgt ccctacaggg cagccccgag    1320
aaccacaggt gtacacctcc ggacatgaaa aaccccaaa taaggaagt ggaaccactt      1380 caggtactac ccgtcttcta tctgggcaca cgtgtttcac gttgacaggt ttgcttggga    1440
cgctagtaac catgggcttg ctgacttaaa ctagtataac ttcgtatagc atacattata    1500
cgaagttata ccctctgccc tgagagtgac cgctgtacca acctctgtcc ctacagggca    1560
gccccgagaa ccacaggtgt acaccctgcc cccatcccgg gatgagctga ccaagaacca    1620
ggtcagcctg acctgcctgg tcaaaggctt ctatcccagc gacatcgccg tggagtggga    1680
gagcaatggg cagccggaga acaactacaa gaccacgcct cccgtgctgg actccgacgg    1740
ctccttcttc ctctacagca agctcaccgt ggacaagagc aggtggcagc aggggaacgt    1800
cttctcatgc tccgtgatgc atgaggctct gcacaaccac tacacgcaga agagcctctc    1860
cctgtctccg ggtaaa                                                    1876
```

<210> SEQ ID NO 17
<211> LENGTH: 1900
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
agcaccaagg gcccatcggt cttccccctg cacctcct ccaagagcac ctctgggggc       60
acagcggccc tgggctgcct ggtcaaggac tacttccccg aaccggtgac ggtgtcgtgg    120
aactcaggcg ccctgaccag cggcgtgcac accttcccgg ctgtcctaca gtcctcagga    180
ctctactccc tcagcagcgt ggtgaccgtg ccctccagca gcttgggcac ccagacctac    240
atctgcaacg tgaatcacaa gcccagcaac accaaggtgg acaagaaagt tggtgagagg    300
ccagcacagg gagggagggt gtctgctgga agccaggctc agcgctcctg cctggacgca    360
tcccggctat gcagcccag tccagggcag caaggcaggc ccgtctgcc tcttcacccg      420
```

```
gaggcctctg cccgccccac tcatgctcag ggagagggtc ttctggctttt ttccccaggc    480 tctgggcagg cacaggctag gtgcccctaa cccaggccct gcacacaaag ggcaggtgc    540 tgggctcaga cctgccaaga gccatatccg ggaggaccct gccctgacc taagcccacc    600 ccaaaggcca aactctccac tccctcagct cggacacctt ctctcctccc agattccagt    660
aactcccaat cttctctctg cagagcccaa atcttgtgac aaaactcaca catgcccacc    720
gtgcccaggt aagccagccc aggcctcgcc ctcagctca aggcgggaca ggtgccctag    780
agtagcctgc atccagggac aggccccagc cgggtgctga cacgtccacc tccatctctt    840
cctcagcacc tgaactcctg gggggaccgt cagtcttcct cttccccca aaacccaagg    900 acaccctcat gatctcccgg acccctgagg tcacatgcgt ggtggtggac gtgagccacg    960
aagaccctga ggtcaagttc aactggtacg tggacggcgt ggaggtgcat aatgccaaga   1020
caaagccgcg ggaggagcag tacaacagca cgtaccgtgt ggtcagcgtc ctcaccgtcc   1080
tgcaccagga ctggctgaat ggcaaggagt acaagtgcaa ggtctccaac aaagcccctcc  1140 cagcccccat cgagaaaacc atctccaaag ccaaaggtgg acccgtggg gtgcgagggc   1200 cacatggaca gaggccggct cggccccata acttcgtata gcatacatta tacgaagtta   1260
taccctctgc cctgagagtg accgctgtac caacctctgt ccctacaggg cagccccgag   1320
aaccacaggt gtacacctcc ggagctgtgg gccaggacac gcaggaggtc atcgtggtgc   1380
cacactcctt gcccttttaag gtggtggtga tctcagccat cctggccctg gtggtgctca   1440
ccatcatctc ccttatcatc ctcatcatgc tttggcagaa gaagcacgt taaactagta   1500 taacttcgta tagcatacat tatacgaagt tataccctct gccctgagag tgaccgctgt   1560
accaacctct gtccctacag gcagccccg agaaccacag gtgtacaccc tgcccccatc   1620
ccgggatgag ctgaccaaga accaggtcag cctgacctgc ctggtcaaag gcttctatcc   1680
cagcgacatc gccgtggagt gggagagcaa tgggcagccg gagaacaact acaagaccac   1740
gcctcccgtg ctggactccg acggctcctt cttcctctac agcaagctca ccgtggacaa   1800
gagcaggtgg cagcagggga acgtcttctc atgctccgtg atgcatgagg ctctgcacaa   1860
ccactacacg cagaagagcc tctccctgtc tccgggtaaa                          1900
```

<210> SEQ ID NO 18
<211> LENGTH: 578
<212> TYPE: DNA
<213> ORGANISM: Unknown
<220> FEATURE:
<223> OTHER INFORMATION: Description of Unknown: Internal
      ribosome entry site polynucleotide

<400> SEQUENCE: 18

```
tccctccccc ccccctaacg ttactggccg aagccgcttg gaataaggcc ggtgtgcgtt    60
tgtctatatg ttatttttcca ccatattgcc gtcttttggc aatgtgaggg cccggaaacc   120
tggccctgtc ttcttgacga gcattcctag ggtctttcc cctctcgcca aggaatgca    180 aggtctgttg aatgtcgtga aggaagcagt tcctctggaa gcttcttgaa gacaaacaac   240
gtctgtagcg acccttttgca ggcagcggaa ccccccacct ggcgacaggt gcctctgcgg   300
ccaaaagcca cgtgtataag atacacctgc aaaggcggca caaccccagt gccacgttgt   360
gagttggata gttgtggaaa gagtcaaatg gctctcctca agcgtattca acaagggct   420 gaaggatgcc cagaaggtac cccattgtat gggatcgat ctggggcctc ggtacacatg   480 cttttacatgt gtttagtcga ggttaaaaaaa acgtctaggc ccccccgaacc acggggacgt   540
```
ggttttcctt tgaaaaacac gatgataata tggccaca 578

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Met Pro Lys Lys Lys Arg Lys
1               5

<210> SEQ ID NO 20
<211> LENGTH: 387
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20
atggacatga gggtccccgc tcagctcctg gggctcctgc tactctggct ccgaggtgcc      60
agatgtgaca tccagatgac ccagtctcca tcctccctgt ctgcatctgt agggacaga     120 gtcaccatca cttgtcgggc aagtcagggc atcagaaatt acttagcctg gtatcagcaa    180
aaaccaggga aagcccctaa gctcctgatc tatgctgcat ccactttgca atcaggggtc    240
ccatctcggt tcagtggcag tggatctggg acagatttca ctctcaccat cagcagccta    300
cagcctgaag atgttgcaac ttattactgt caaaggtata accgtgcacc gtatactttt    360
ggccagggga ccaaggtgga aatcaaa                                        387

<210> SEQ ID NO 21
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Tyr Leu Ala Trp Tyr Gln Lys Pro Gly Lys
    50                  55                  60

Ala Pro Lys Leu Leu Ile Tyr Ala Ala Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Val Ala Thr Tyr Tyr Cys Gln Arg
            100                 105                 110

Tyr Asn Arg Ala Pro Tyr Thr Phe Gly Gln Gly Thr Lys Val Glu Ile
        115                 120                 125

Lys

```
<210> SEQ ID NO 22
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atggagtttg ggctgagctg gcttttctt  gtggctattt  taaaaggtgt  ccagtgtgag      60
gtgcagctgg tggagtctgg gggaggcttg gtacagcccg gcaggtccct gagactctcc     120
tgtgcggcct ctggattcac ctttgatgat tatgccatgc actgggtccg gcaagctcca     180
gggaagggcc tggaatgggt ctcagctatc acttggaata gtggtcacat agactatgcg     240
gactctgtgg agggccgatt caccatctcc agagacaacg ccaagaactc cctgtatctg     300
caaatgaaca gtctgagagc tgaggatacg gccgtatatt actgtgcgaa agtctcgtac     360
cttagcaccg cgtcctccct tgactattgg ggccaaggta ccctggtcac cgtctcgagt     420
gct                                                                   423

<210> SEQ ID NO 23
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

Asp Asp Tyr Ala Met His Trp Val Arg Gln Ala Pro Gly Lys Gly Leu
        50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala
    130                 135                 140
```

CELL LINE SCREENING METHOD

CROSS-REFERENCE TO RELATED APPLICATIONS

This application claims the priority benefit of U.S. provisional application No. 61/732,156, filed Nov. 30, 2012, which is expressly incorporated by reference herein in its entirety.

The present technology pertains to cell line development and protein production, and more specifically to a switch mechanism that converts cells that express a membrane-anchored reporter (MAR) into production cells that secrete a protein of interest (POI) into culture media.

BACKGROUND

Recombinant therapeutic proteins are widely used to treat numerous human diseases from cancer to infertility. They include various blood-clotting factors, insulin, growth hormones, enzymes, Fc fusion proteins, monoclonal antibodies and other proteins (Scott C., Bioprocess Int. 10(6): S72-S78, 2012). Many recombinant therapeutic proteins are manufactured using mammalian host cells because of the need for correct folding and post-translational modification including glycosylation. Among them, therapeutic antibodies represent one of the largest sectors of protein therapeutics with a global market of approximately $50 billion in 2011 for approximately 30 approved antibody therapeutics.

The predominant therapeutic antibodies come from antibody discovery programs that belong to four categories: chimeric antibodies, humanized antibodies, fully human antibodies from synthetic human antibody libraries selected with various display systems, and fully human antibodies from transgenic animals bearing human immunoglobulin genes (Chames P. et al, Br J Pharmacol. 157(2): 220-233, 2009). Chimeric antibodies containing human constant regions and non-human variable regions pose an immunogenicity risk in the human body and as a result have lost favor to humanized or fully human antibodies in terms of therapeutic applications. Humanized antibodies contain 90-95% human residues and 5-10% non-human residues that are essential for antigen interaction, whereas fully human antibodies contain 100% human residues. Both humanized and fully human antibodies have enjoyed great success in therapeutic applications to treat various diseases.

Development of a therapeutic antibody often takes 10-15 years including antibody discovery, engineering, production cell line development, manufacturing process development, and clinical studies. Among these tasks, antibody discovery may take 6-18 months and production cell line development may require an additional 6-10 months. One of the biggest problems with current antibody discovery methodologies is that they do not utilize the format of the final antibody product which is commonly a full-length human IgG. The selected antibodies are typically murine antibodies or fragments of human antibodies such as scFv or Fab, that require reformatting into the final IgG format before production cell line development. Reformatting sometimes leads to unexpected problems in downstream process development, including loss of activity, low expression level, aggregation, insolubility, and/or instability. Therefore further antibody engineering and optimization may be required, resulting in loss of valuable time and increased cost.

Cell line development is a critical part of the process to obtain production cell lines for any therapeutic protein including antibodies. Production cell lines should be highly productive, stable, and have correct product quality attributes including biological activity, protein sequence homogeneity, glycosylation profile, charge variants, oxidation, deamination and low levels of aggregation. CHO cells are the most popular mammalian cells for production of therapeutic proteins. Other mammalian cells like NS0 or SP2/0 cells have also been used to produce biological therapeutics (Jayapal K R, et al., Chemical Engineering Progress, 103: 40-47, 2007; Li F, et al., MAbs. 2(5): 466-477, 2010). Conventional cell line development utilizes gene amplification systems by incorporating Dihydrofolate Reductase (DHFR) or Glutamine Synthetase (GS) as selection markers. Typically up to 1000 clones are screened in a cell line development program by limiting dilution cloning in 96-well tissue culture plates. Obtaining a highly productive cell line requires gene amplification by adding selection pressure after stable transfection using, for example, Methotrexate (MTX) in the DHFR system, or Methionine Sulphoximine (MSX) in the GS system. In most cases, productivity is often the only selection criteria until a very late stage in the process when only a handful of clones are assessed for the other quality attributes important for large scale manufacturing, resulting in increased project risk and complex issues regarding downstream development.

The process of selecting a cell population of interest for use as a recombinant protein production cell line may involve expression of a cell surface or intracellular reporter molecule. High level of expression of intracellular reporters such as GFP have been shown to be cytotoxic (Liu H S, et al., Biochem Biophys Res Commun, 260: 712-717, 1999; Wallace L M, et al., Molecular Therapy Nucleic Acids. 2, e86, 2013), however, the cytotoxicity of a reporter is minimized by cell surface display.

Display techniques have been developed for high-throughput screening of proteins, such as antibodies. Antibody display systems have been successfully applied to screen, select and characterize antibody fragments. These systems typically rely on phage display, *E. coli* display or yeast display. Each display system has its strengths and weaknesses, however, in general these systems lack post-translational modification functions or exhibit different post-translational modification functions from mammalian cells and tend to display small antibody fragments instead of full-length IgGs. Thus, characterization of the biological activities and further development of the isolated antibody fragments often requires conversion to whole immunoglobulins and expression in mammalian cells for proper folding and post-translational processing. This conversion process may produce antibodies with binding characteristics unlike those selected for in the initial screen.

There is a need for improved processes for selection of recombinant protein producing cell lines (such as antibody-producing cell lines), wherein the selection process facilitates rapid cell line selection based on quality attributes other than productivity. The present invention provides improved compositions and methods for screening and selection of cell lines for recombinant protein production.

SUMMARY OF THE INVENTION

Additional features and advantages of the disclosure will be set forth in the description which follows, and in part will be obvious from the description, or can be learned by practice of the herein disclosed principles. The features and advantages of the disclosure can be realized and obtained by means of the disclosure and examples provided herein. These and other features of the invention will become more fully apparent from the following description and appended claims, or can be learned by the practice of the principles set forth herein.

The present invention relates to a switch mechanism that may turn off expression of a reporter (e.g., a cell surface or intracellular reporter) after selection of a subpopulation of cells providing for optimal expression of a POI. The reporter can be GFP or any other molecule detectable by FACS, MACS, or any other analytic method effective to detect the reporter. Expression of the reporter is functionally linked to expression of a POI such that the reporter is a surrogate for POI expression. The above-mentioned switch mechanism maybe used to turn cells displaying a cell surface membrane anchored reporter (MAR) or intracellular reporter into production cells secreting a POI. Disclosed are a series of molecular designs which incorporate sequences of MAR flanked by site-specific DNA recombinase recognition sequences (DRRS) inserted into an expression vector for a gene of interest (GOI). The reporter cassette could reside between the promoter and the GOI or downstream of the GOI following an internal ribosome entry site (IRES) or another promoter. In both cases, reporter expression will be first allowed to facilitate cell selection by FACS or MACS and then eliminated by transient expression or direct provision of an appropriate site-specific DNA recombinase to the cells in order to switch the cells to produce the POI without co-expression of the reporter.

Alternatively, the reporter cassette could reside in the middle of an intron sequence of the GOI to create alternative splicing leading to expression of the reporter. After transient expression or direct provision of an appropriate site-specific DNA recombinase protein, the reporter cassette is deleted from the intron enabling optimal expression and secretion of the POI without co-expression of the reporter.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings.

DETAILED DESCRIPTION OF THE INVENTION

Figure 1A:
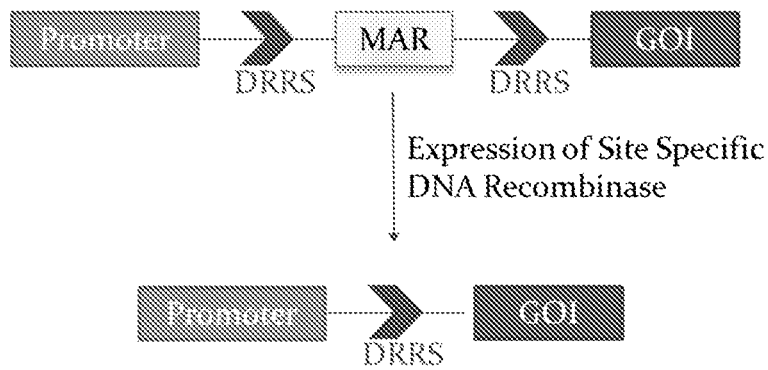
FIGS. 1A-C are schematic drawings of exemplary MAR cassettes containing expression vectors and the switch mechanism that deletes the MAR. The MAR resides before the GOI (in A), or after the GOI following an IRES or another promoter (in B), or in the middle of an intron of the GOI (in C).

Provided herein are compositions, methods and systems for improved selection of production cells that secrete a protein of interest (POI) into culture media.

The invention is not limited to the specific compositions, devices, methodology, systems, kits or medical conditions described herein, as such may, of course, vary. It is also to be understood that the terminology used herein is for the purpose of describing particular embodiments only, and is not intended to limit the scope of the present invention.

The present invention concerns a switch mechanism that can be used to turn cells expressing a membrane-anchored reporter (MAR) or an intracellular reporter into production cells secreting a protein of interest (POI) into culture media, e.g., an antibody or any other protein. The MAR can be any molecule including a membrane-anchored POI, a membrane-anchored GFP, or any other membrane associated molecule which can be detected or selected using high throughput methodologies such as fluorescence-activated cell sorting (FACS) or magnetic-activated cell sorting (MACS), or any other analytic method effective to detect expression of the reporter molecule. The method allows for initial screening or selection of desired cells using methodologies such as FACS or MACS by detecting a reporter molecule, followed by application of a molecular switch that transforms the cells such that they secrete the POI without co-expression of the reporter molecule for production purposes.

Various embodiments of the disclosure are discussed in detail below. While specific embodiments are discussed, it should be understood that this is done for illustration purposes only. A person skilled in the relevant art will recognize that other configurations may be used without departing from the spirit and scope of the disclosure.

Definitions

It must be noted that as used herein and in the appended claims, the singular forms "a", "and", and "the" include plural references unless the context clearly dictates otherwise.

Unless defined otherwise, all technical and scientific terms used herein generally have the same meaning as commonly understood to one of ordinary skill in the art to which this invention belongs.

The publications discussed herein are provided solely for their disclosure prior to the filing date of the present application. Nothing herein is to be construed as an admission that the invention is not entitled to antedate such a disclosure by virtue of prior invention.

As used herein, the term "membrane-anchored reporter" or "MAR" is used with reference to any membrane molecule or a non-membrane molecule fused with a membrane association domain (MAD).

As used herein, the term "membrane association domain" or "MAD" is used with reference to a protein domain associated with a membrane, which could be a GPI anchor signal sequence (GASS), a transmembrane domain, or any molecule that binds to a cell membrane or a membrane protein e.g., an Ab, GFP, and the like. In one aspect of the invention a host cell is characterized by the expression of a cell surface membrane anchored reporter fused to a POI wherein expression of the reporter is detected by FACS, MACS or any technique that can detect cell surface expression of a POI. Expression of the cell surface membrane anchored reporter fused to a POI is detected following transfection with a DNA construct such as shown in FIGS. 3A-D, 6A and B.

As used herein, the term "protein of interest" or "POI" is used with reference to a protein having desired characteristics that may be selected using the method of the invention. A "protein of interest" (POI) includes full length proteins, polypeptides, and fragments thereof, peptides, all of which can be expressed in the selected host cell. Exemplary POIs are antibodies, enzymes, cytokines, adhesion molecules, receptors, derivatives and any other polypeptides that can be expressed using the methods described herein. In another aspect of the invention, the protein of interest is recovered from the culture medium as a secreted polypeptide. In general, the protein of interest is produced in the culture media at a level of at least 100 mg/L, at least 150 mg/L, at least 200 mg/L, at least 300 mg/L, at least 500 mg/L, at least, or at least 1000 mg/L, e.g., 100-150 mg/L, 150-200 mg/L, 200-250 mg/L, 250-300 mg/L, 300-500 mg/L, or 500-1000 mg/L. In some cases, the POI, e.g., an enzyme, may be biologically active a low concentration. In such cases, production at a level below 100 mg/L in the culture media will satisfy commercial production requirements. In general, methods teaching a skilled person how to purify a protein expressed by host cells are well known in the art.

As used herein, the term "gene of interest" or "GOI" is used with reference to a polynucleotide sequence of any length that encodes a "protein of interest" (POI). The selected sequence can be full length or a truncated gene, a fusion or tagged gene, and can be a cDNA, a genomic DNA, or a DNA fragment, preferably, a cDNA. It can be the native sequence, i.e. naturally occurring form(s), or can be mutated or otherwise modified as desired.

The term "host cells" or "expression host cells" as used herein refers to any cell line that will effectively produce a POI with correct folding and post-translational modification including glycosylation as required for biological activity. Exemplary host cells include Chinese Hamster Ovary (CHO) cells, e.g., CHOS (Invitrogen), NSO, Sp2/0, CHO derived mutant cell or derivatives or progenies of any of such cells. Other mammalian cells, including but not limited to human, mice, rat, monkey, and rodent cells, and eukaryotic cells, including but not limited to yeast, insect, plant and avian cells, can also be used in the meaning of this invention, as appropriate for the production of a particular POI.

As used herein, the term "magnetic-activated cell sorting" or "MACS" is used with reference to a method for separation of various cell populations depending on their surface antigens (CD molecules). The term MACS is a registered trademark of Miltenyi Biotec and the method is marketed by the company as MACS Technology.

As used herein, the term "DNA recombinase recognition sequence" or "DRRS" is used with reference to a sequence that facilitates the rearrangement of DNA segment by the activity of a site-specific recombinase which recognizes and binds to short DNA sequences resulting in cleavage of the DNA backbone such that two DNA sequences are exchanged, followed by rejoining of the DNA strands.

As used herein, the term "GPI anchored signal sequence" or "GASS" is used with reference to a glycolipid that can be attached to the C-terminus of a protein during posttranslational modification. It is composed of a phosphatidylinositol group linked through a carbohydrate-containing linker (glucosamine and mannose glycosidically bound to the inositol residue) to the C-terminal amino acid of a mature protein. The hydrophobic phosphatidyl-inositol group anchors the protein to the cell membrane.

The term "productivity" or "specific productivity" describes the quantity of a specific protein (e.g., a POI) which is produced by a defined number of cells within a defined time. One exemplary way to measure "productivity" is to seed cells into fresh culture medium at defined densities. After a defined time, e.g. after 24, 48 or 72 hours, a sample of the cell culture fluid is taken and subjected to ELISA measurement to determine the titer of the protein of interest. The productivity can be reported as mg/L of culture media. In the context of industrial manufacturing, the specific productivity is usually expressed as amount of protein in picogram produced per cell and day ("pg/cell/day").

The term "biological activity" describes and quantifies the biological functions of the protein within the cell or in in vitro assays.

Description

The present invention relates to a series of molecular designs incorporating sequences of a membrane-anchored reporter (MAR) or an intracellular reporter flanked by site specific DNA recombinase recognition sequences (DRRS) inserted into an expression vector for the GOI. The reporter cassette could reside between the promoter and the GOI (FIG. 1A), or after the GOI following an IRES or another promoter (FIG. 1B), or in the middle of an intron of the GOI (FIG. 1C). The reporter is first expressed allowing cell selection e.g., by FACS or MACS, and then deleted by transient expression or direct provision of an appropriate site-specific DNA recombinase to switch the cells to secretion of the POI without co-expression of the reporter. The MAR needs to be detected or selected using high throughput methodologies such as FACS or MACS, and could be any membrane protein or non-membrane protein fused with a membrane association domain (MAD), which could be a GPI anchor signal sequence (GASS), or a transmembrane domain, or any peptide that binds to a cell surface protein. For example, the MAR could be membrane-anchored GFP or membrane-anchored POI. One of the advantages of using a membrane anchored reporter protein instead of an intracellular reporter protein is to avoid any potential cellular toxicity after accumulation of high concentrations of the reporter protein. SEQ ID NO: 1 shows the nucleotide sequence of GFP fused to the IL2 signal peptide at the N-terminus and DAF GASS at the C-terminus. Any GFP variants or other fluorescent proteins, functional signal peptides or membrane association domains can be used here.

After being transfected with reporter-containing expression vectors, the host cells such as CHO cells can be allowed to grow in the presence of appropriate antibiotics for selection of stable cells with the expression vector integrated into the chromosome. Alternatively, the transfected cells can be selected directly for the reporter expression by FACS or MACS for 1-2 weeks until the reporter expression is stable. The advantage of not using antibiotics is for better health of the cells and potentially less gene-silencing of the expression cassette (Kaufman W L, et al., Nucleic Acids Res., 36(17), e111, 2008). Desired cells with high expression levels of the reporter or other properties (such as stability, protein sequence homogeneity, proper glycosylation profile, proper charge variants, and acceptable aggregate levels), can then be selected with FACS or MACS or another analytic technique. Subsequently the reporter cassette can be deleted by providing an appropriate site-specific DNA recombinase to switch the selected cells into production cells that produce the POI. The DNA recombinase can be supplied to the cells by transient transfection with an expression vector, or by direct provision of the DNA recombinase protein to the culture media, or by any other means.

Figure 2:
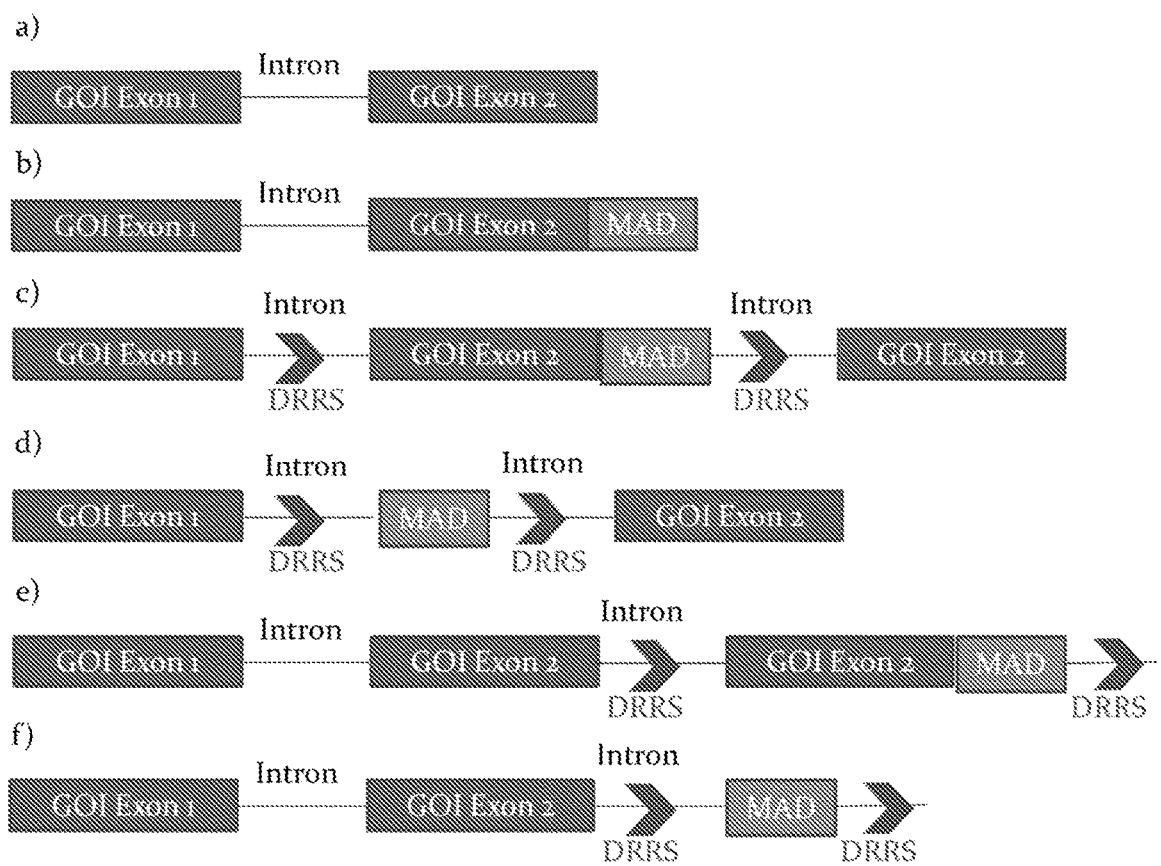
FIG. 2 views a-f are schematic drawings of exemplary molecular structures of a model GOI, including a) a wild-type genomic sequence with one intron and two exons; b) the exon 2 fused with a membrane association domain (MAD); c) insertion of Exon 2-MAD flanked by site specific DNA recombinase recognition sequences (DRRS) in the intron; d) insertion of MAD flanked by DRRS into the intron; e) insertion of Exon 2-MAD flanked by site specific DNA recombinase recognition sequences (DRRS) downstream of Exon 2 and f) insertion of MAD flanked by DRRS downstream of Exon 2.

The present invention also provides a series of molecular designs to modify the intron sequence of a GOI. FIG. 2A shows the genomic sequence of a model secreted GOI containing two exons and an intron. It would be anchored on cell surface if fused with a MAD, which could be a GASS, or a transmembrane domain, or any peptide that binds to a cell surface protein (FIG. 2B). In order to create an alternative splicing site, the DNA sequence of GOI Exon 2 fused with MAD flanked by DRRS can be inserted into the Intron (FIG. 2C), MAD flanked by DRRS can be inserted into the Intron (FIG. 2D), the DNA sequence of GOI Exon 2 fused with MAD flanked by DRRS can be inserted downstream of Exon 2 (FIG. 2E), or MAD flanked by DRRS can be inserted downstream of Exon 2 (FIG. 2F).

Figure 3A:
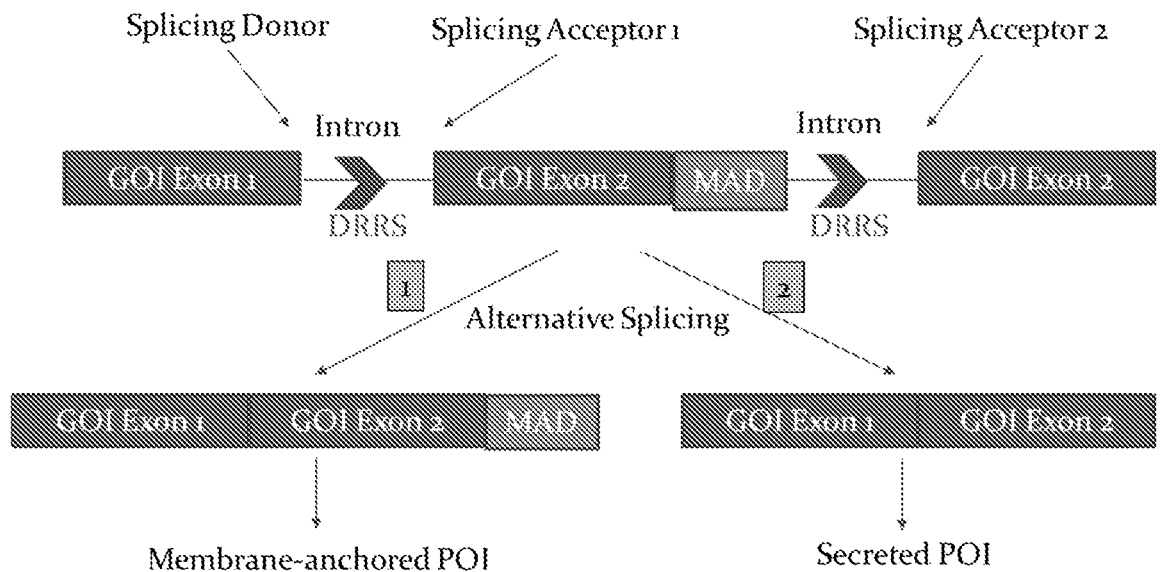
FIGS. 3A, 3B, 3C and 3D are schematic drawings of two alternative RNA splicing events of the molecular design in FIG. 2C (3A), FIG. 2D (3B), FIG. 2E (3C) and FIG. 2F (3D).
Figure 3B:
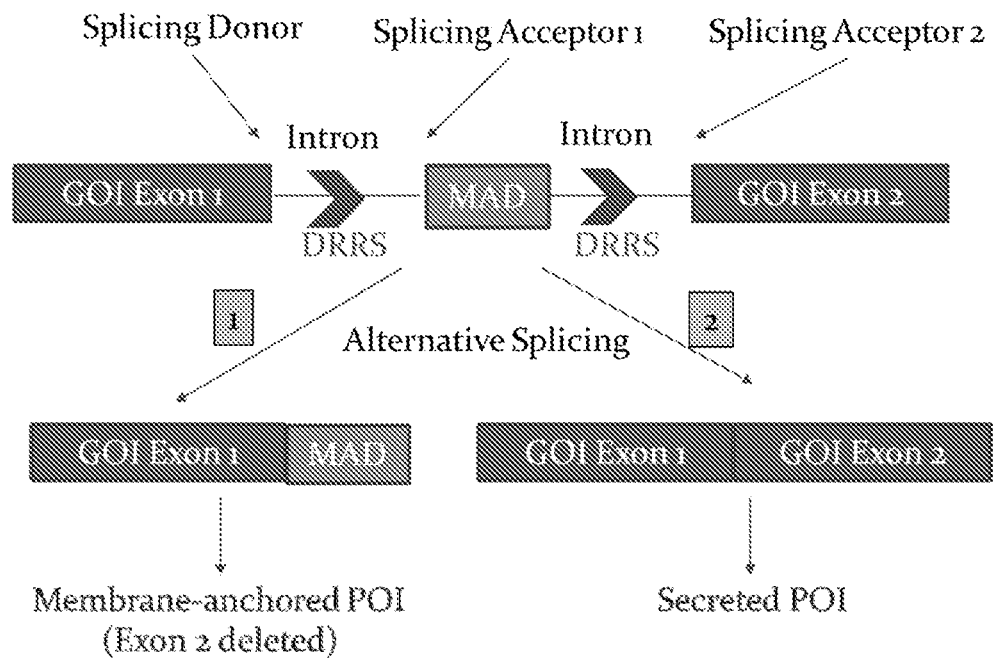
Figure 3C:
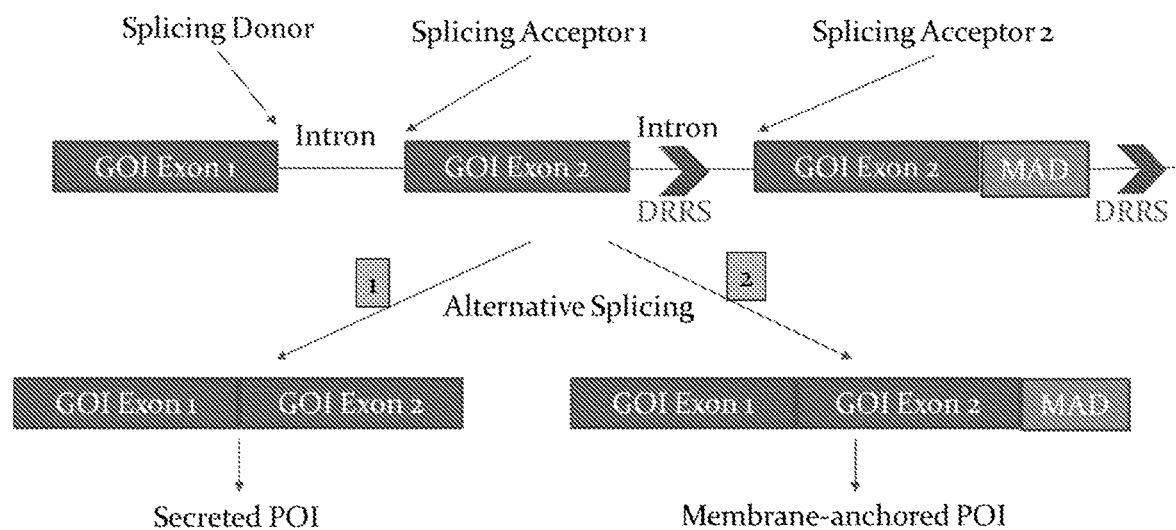
Figure 3D:
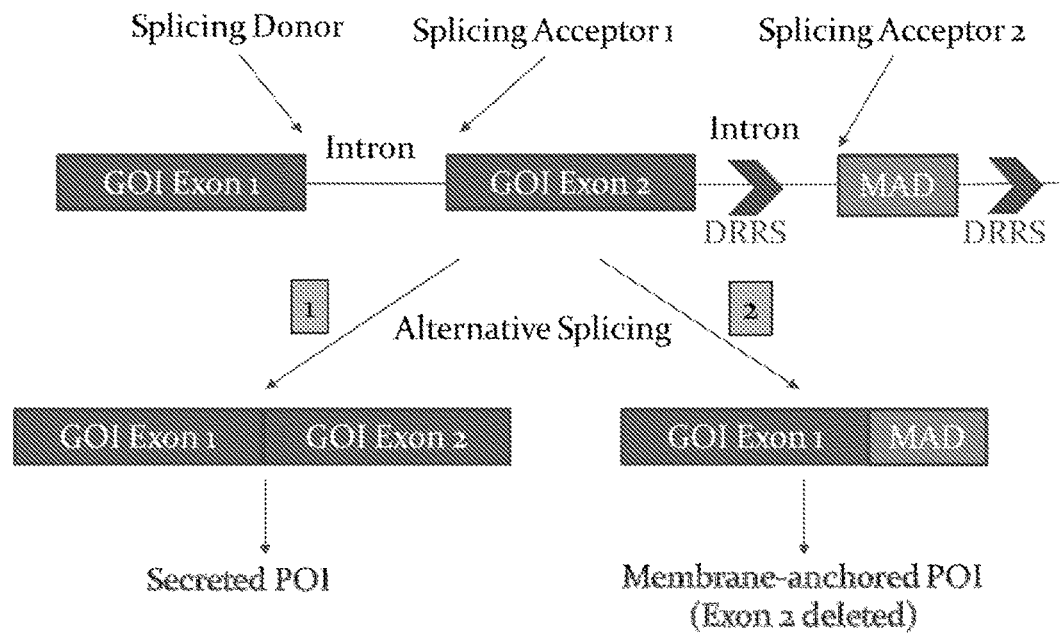
Figure 4A:
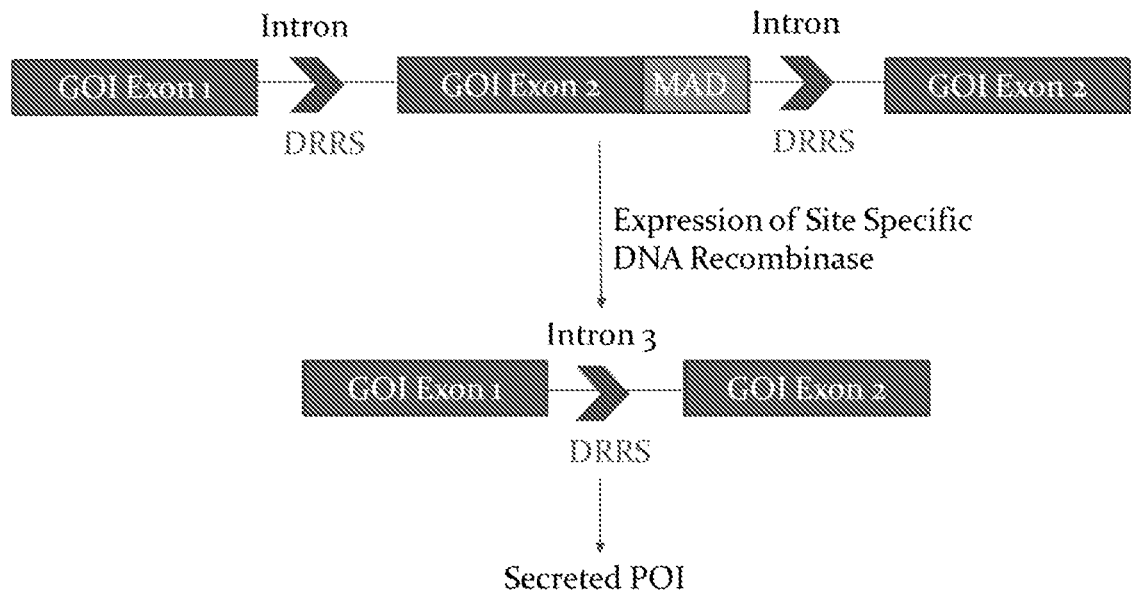
FIG. 4A-D are schematic drawings of DNA recombination in the presence of an appropriate site specific DNA recombinase of the molecular design in FIG. 2C (4A), FIG. 2D (4B), FIG. 2E (4C) and FIG. 2F (4D).

The mRNA may contain an unaltered splicing donor or any functional splicing donor for the Intron and two splicing acceptors shown in FIG. 3A. The two splicing acceptors may be identical to the splicing acceptor in the wild type GOI mRNA or any functional splicing acceptor. This exemplary alternative splicing would lead to membrane-anchored POI using the acceptor 1 or secreted POI using the acceptor 2 (FIG. 3A). If only secreted POI is desired, appropriate site-specific DNA recombinase recognizing the DRRS can be transiently expressed in the cell and the sequence between the DRRS deleted as shown in FIG. 4A.

Figure 4B:
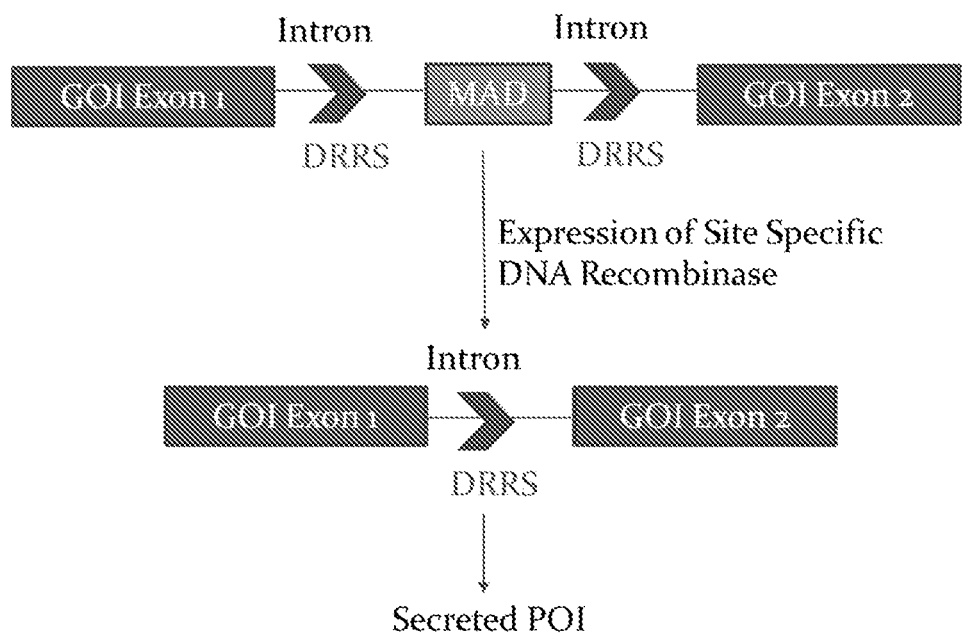

Another way to manipulate the Intron is to insert a MAD sequence flanked by DRRS directly (FIG. 2D). Alternative splicing shown in FIG. 3B would lead to either membrane-anchored POI with Exon 2 deleted or secreted POI. When an appropriate site-specific DNA recombinase is supplied, the sequence between DRRS is deleted and all the expressed POI is secreted (FIG. 4B).

Figure 4C:
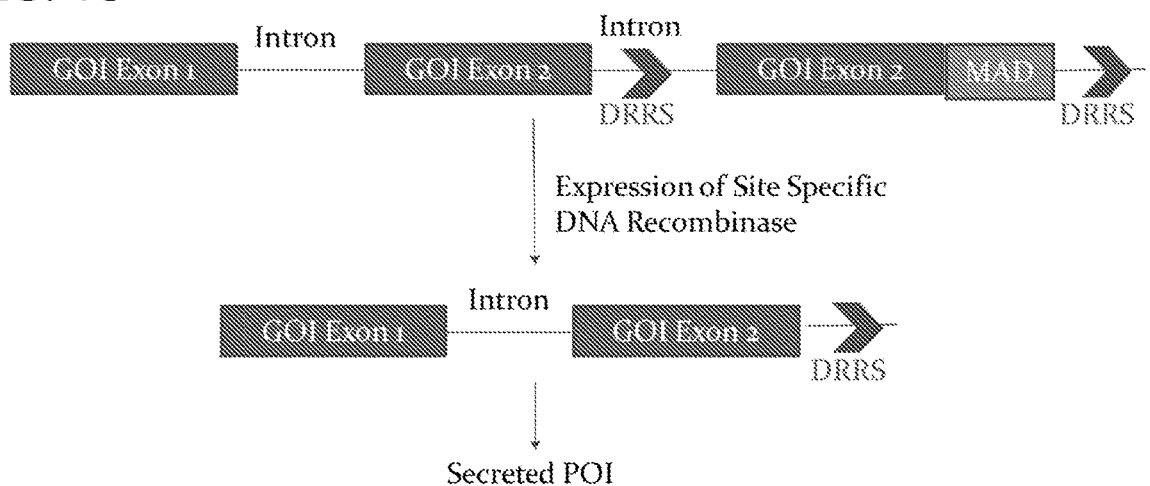

Yet another way to manipulate the Intron is to insert Exon-2-MAD flanked by site specific DNA recombinase recognition sequences (DRRS) downstream of Exon 2 (FIG. 2E). Alternative splicing shown in FIG. 3C would lead to either membrane-anchored POI with Exon-1 and Exon-2 fused to MAD, or secreted POI with Exon1 and Exon2. When an appropriate site-specific DNA recombinase is supplied, the sequence between DRRS is deleted and all the expressed POI is secreted (FIG. 4C).

Figure 4D:
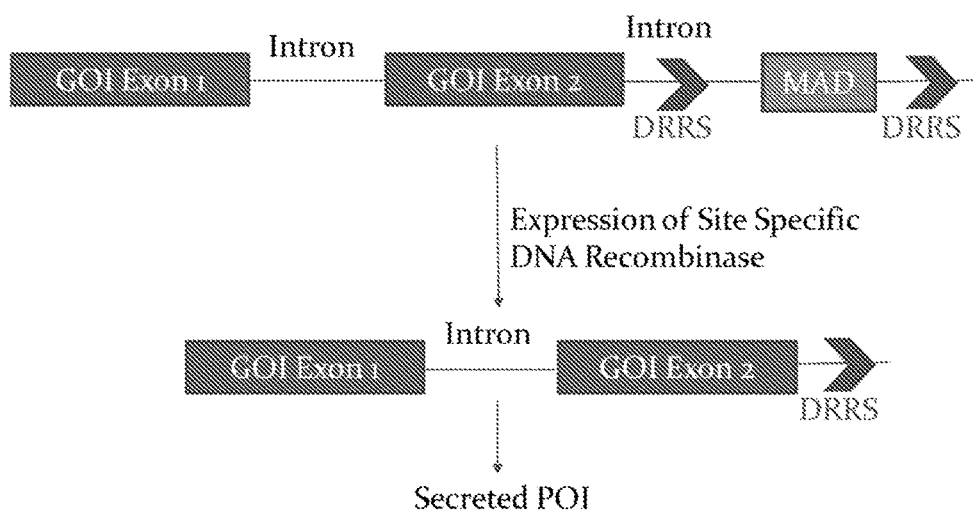

A further way to manipulate the Intron is to insert a MAD sequence flanked by DRRS downstream of Exon 2 (FIG. 2F). Alternative splicing shown in FIG. 3D would lead to either membrane-anchored POI with Exon 2 deleted, or secreted POI with Exon1 and Exon2. When an appropriate site-specific DNA recombinase is supplied, the MAD sequence between DRRS is deleted and all the expressed POI is secreted (FIG. 4D).

Figure 5:
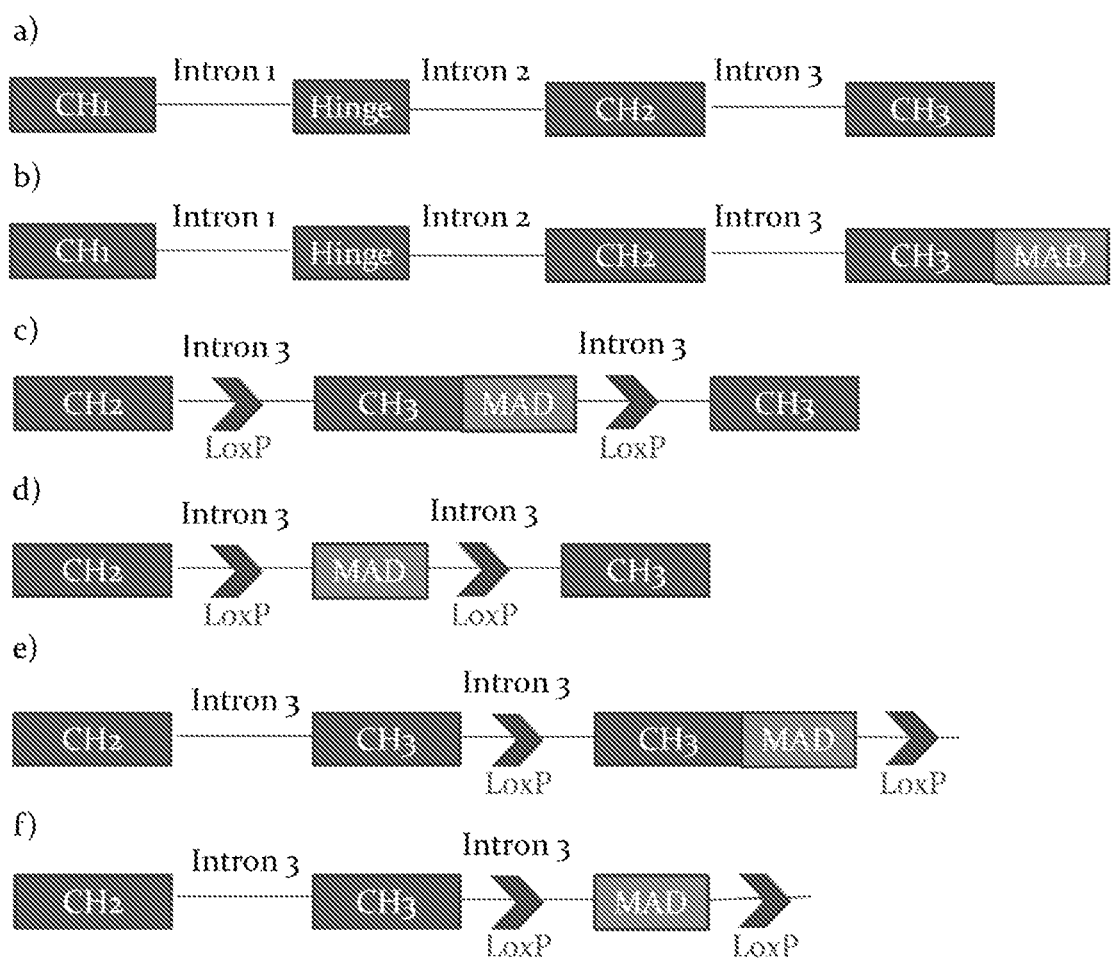
FIG. 5 views a-f are schematic drawings of exemplary antibody heavy chain genomic sequences. a) Wild-type heavy chain constant region, including four exons (CH1, Hinge, CH2, and CH3) and three introns (Intron 1-3); b) The heavy chain fused with a MAD; c) Insertion of CH3-MAD flanked by LoxP sequences into the Intron 3; d) Insertion of MAD flanked by LoxP sequences into the Intron 3; e) Insertion of CH3-MAD flanked by LoxP sequences downstream of CH3; and f) Insertion of MAD flanked by LoxP sequences downstream of CH3. Regions before CH2 are present but not shown in c)-f).

FIGS. 5-7 describe how the above-mentioned intron modifying designs are applied to manipulate a human immunoglobulin gamma genomic sequence. The genomic structure of the wild-type human antibody IgG1 heavy chain constant region contains four exons and three introns as shown in FIG. 5A. The DNA sequence is shown in SEQ ID NO: 3. FIG. 5B shows a membrane-anchored antibody heavy chain prepared by fusing with a MAD. It has been reported that membrane-anchored antibodies can be constructed by fusing a GASS or a transmembrane domain (TM) at the C-terminus of the heavy chain (Zhou C, et al., MAbs, 2:508-518, 2010; Bowers P M, et al. Proc Natl Acad Sci USA, 108(51):20455-20460, 2011; Li. F, et al., Appl Microbiol Biotechnol., 96(5):1233-41 2012). The GASS of human DAF is shown in SEQ ID NO: 4 (nucleotide) and SEQ ID NO: 5 (amino acid), respectively. Any other GASS or TM or any peptide that binds to a cell surface protein can also be used for membrane anchoring. In order to create an alternative splicing site, the DNA sequence for CH3-MAD flanked by DRRS can be inserted into Intron 3 (FIG. 5C), or into the other two introns; the DNA sequence for MAD flanked by DRRS can be inserted into Intron 3 (FIG. 5D), the DNA sequence for CH3-MAD flanked by LoxP sequences may be inserted downstream of Exon 3 (FIG. 5E) or the DNA sequence for MAD flanked by LoxP sequences may be inserted downstream of Exon 3 (FIG. 5F).

Figure 6A:
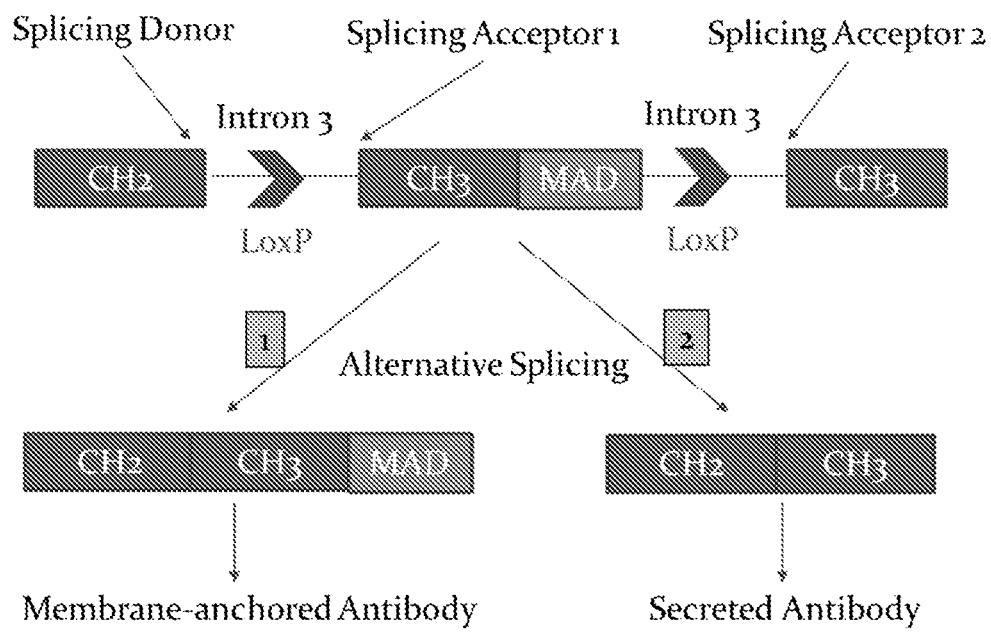
FIGS. 6A and B are schematic drawings of two alternative RNA splicing events of the molecular designs in FIG. 5C (6A) and FIG. 5D (6B). Regions before CH2 are not shown.

One commonly used recognition sequence for DNA recombinase Cre is LoxP the sequence of which is shown in SEQ ID NO: 8. Similarly, any other LoxP variant sequences or recognition sequences for other site specific DNA recombinases can be used here, for example, an FRT sequence (DRRS for FLP), or an attB or attP (DRRS for φC31 integrase (Wang Y, et al., Plant Cell Rep.; 30(3):267-85, 2011) or a specific DNA recognition sequence for any other tyrosine recombinase or serine recombinase. The mRNA may have an unaltered splicing donor for the Intron 3 and two identical splicing acceptors as shown in FIG. 6A.

Figure 7A:
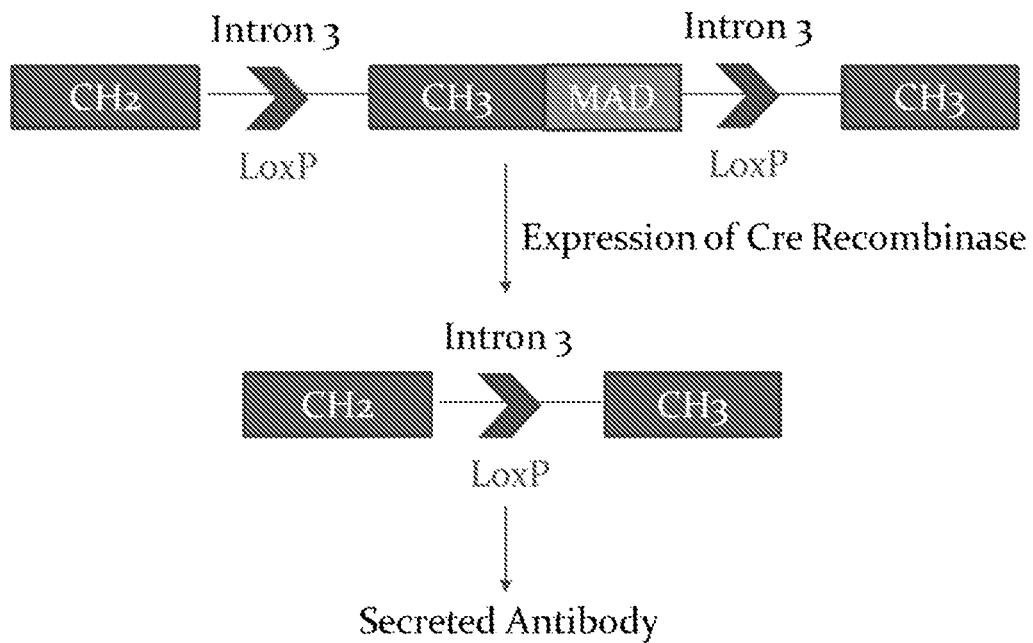
FIGS. 7A and B are schematic drawings of DNA recombination in the presence of Cre recombinase of the molecular designs in FIG. 5C (7A) and FIG. 5D (7B). Regions before CH2 are not shown.

The alternative splicing would lead to membrane-anchored antibody using the acceptor 1 or secreted antibody using the acceptor 2. If only secreted antibody is desired, DNA recombinase Cre can be transiently expressed in the cell or supplied in the culture media and the sequence between the two LoxP sites will be deleted as shown in FIG. 7A.

Figure 6B:
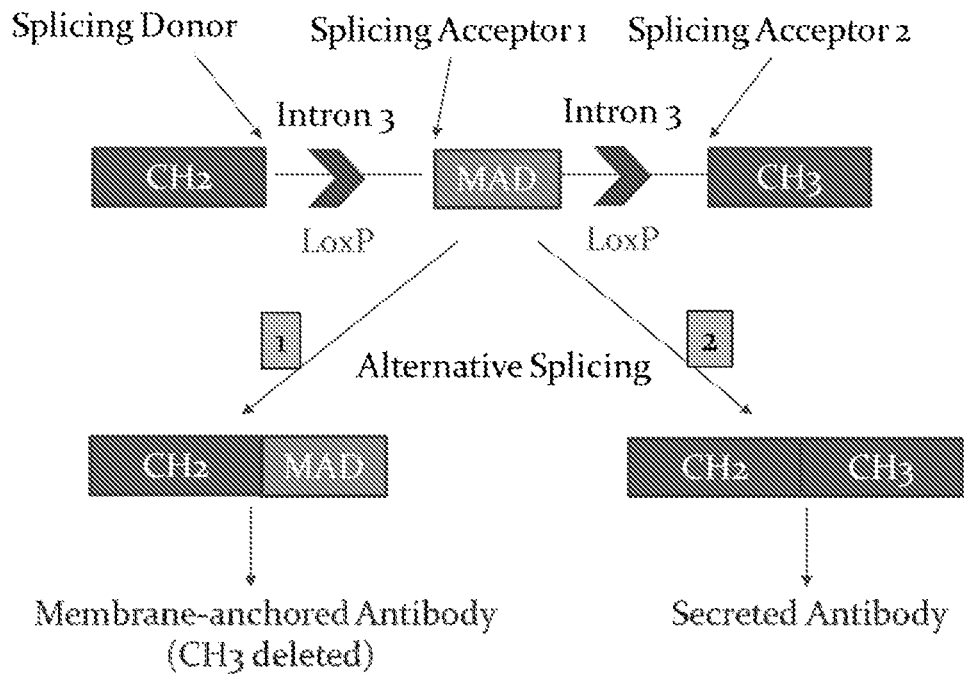
Figure 7B:
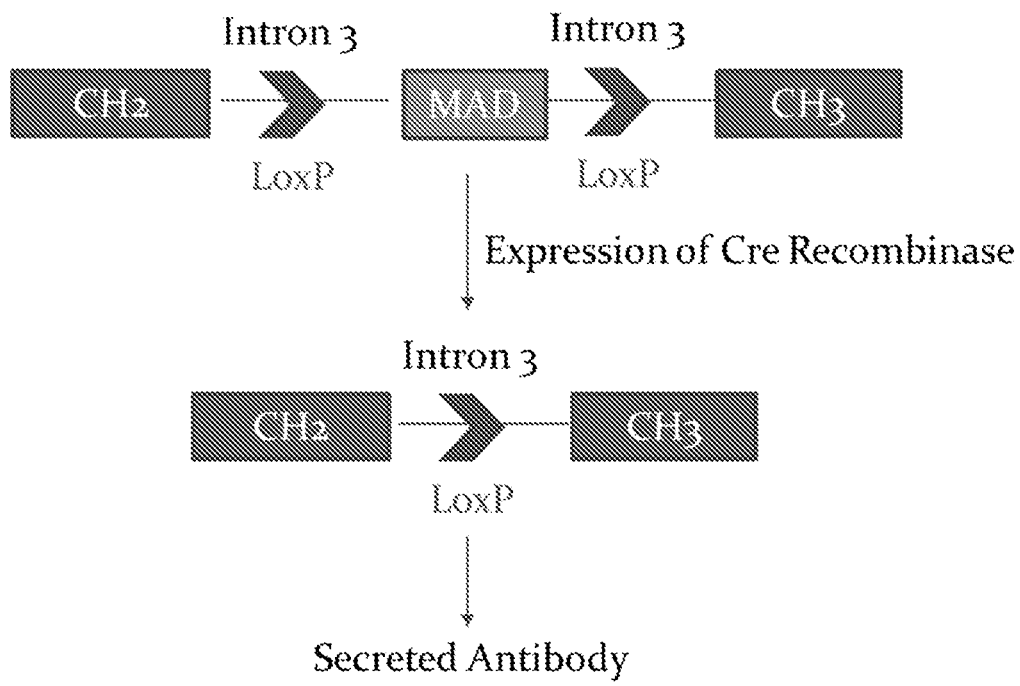

For example, if one were to manipulate Intron 3 is to insert a DNA sequence for MAD flanked by LoxP sites directly (FIG. 5D), alternative splicing shown in FIG. 6B would give membrane-anchored antibody with CH3 deleted or secreted antibody. When DNA recombinase Cre is expressed, the sequence between LoxP sites is deleted and all the expressed antibody is secreted (FIG. 7B). Similarly, the MAD flanked by LoxP sites can also be inserted into the other two introns to create alternative splicing.

Figure 8A:
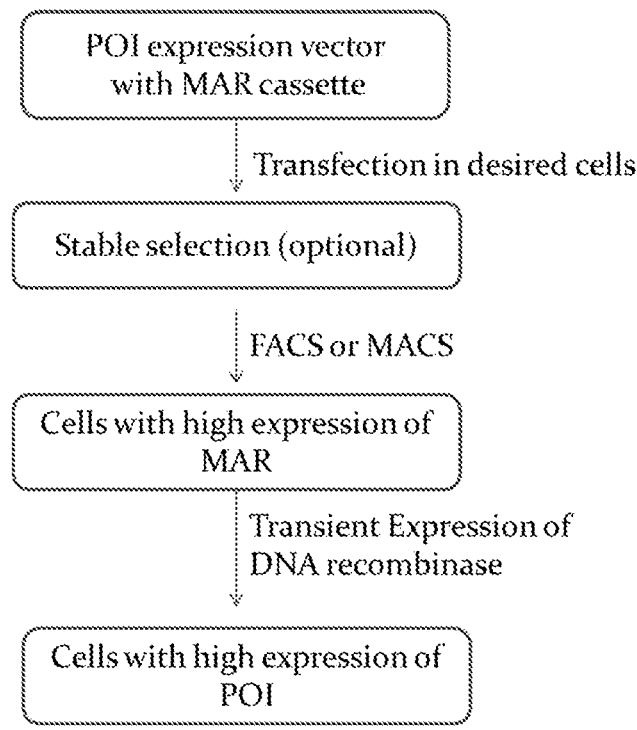
FIGS. 8A and B are flow charts of an antibody cell line development process (8A) and an antibody library screening process (8B).

FIG. 8A illustrates an exemplary cell line development process utilizing the MAR cassette and the switching mechanism. Expression vector of the GOI is modified with the MAR cassette as shown in FIG. 1. It could carry a selection marker gene. If the POI contains more than one subunit, they may be cloned into the same vector or into separate expression vectors. The expression vector or vectors are transfected into desired cells. After 1-2 weeks allowing stable integration into the chromosome, with or without antibiotic selection, the cells are analyzed and selected for high expression of the MAR by any high throughput cell selection or enrichment methodology, such as FACS or MACS. In one approach, the selected cells are transfected transiently with an expression vector for an appropriate DNA recombinase to induce site-specific DNA recombination. Deletion of the MAR cassette results in cells that produce the POI. Following single cell sorting or limiting dilution cloning into 96-well plates, clones are screened for the POI expression levels in the culture media and/or other desired product quality attributes. Selected clones are expanded and cryopreserved.

In one application of the invention, an human immunoglobulin gamma expression vector comprising a membrane association domain (MAD) flanked by site specific DNA recombinase recognition sequences (DRRS) can be inserted into the intron region between CH2 and CH3 sequences. The MAD can be a GPI anchored signal sequence (GASS) or a transmembrane domain or a peptide that binds to any cell surface protein. Alternative splicing results in a portion of expressed antibodies to be membrane-anchored and thus readily detected by fluorescence-labeled antigen or secondary antibody. After selection of cells with high expression levels of membrane-anchored antibodies by FACS, the cells may then be switched into production cells secreting the antibody into culture media by transient expression of an appropriate site-specific DNA recombinase in order to delete the sequences responsible for membrane association in the intron. The switch mechanism can be used for cell line development with greatly reduced time and cost, and can be used for production of antibody or any other recombinant protein.

Library display techniques have been developed for high-throughput screening of proteins having desired characteristics. WO 2010/022961 discloses a method for generating or selecting a eukaryotic host cell expressing a desired level of a polypeptide of interest from a population of host cells by use of a fusion polypeptide including an immunoglobulin transmembrane anchor such that the fusion polypeptide is being displayed on the surface of the host cell.

Bowers P M, et al. (Proc Natl Acad Sci USA. 108(51): 20455-60, 2011) disclose a method for the isolation of human antibodies using a library screening method based on initial selection of well-expressed human IgM antibodies with high binding affinity by FACS, followed by activation-induced cytidine deaminase (AID) directed in vitro somatic hypermutation (SHM) in vitro and selection of high-affinity antibodies using the same library screening method.

DuBridge et al. U.S. Pat. No. 7,947,495, disclose dual display vector compositions and methods which provide for expression of secreted and membrane-bound forms of an immunoglobulin based on splice sites and recombinase recognition sites, allowing for simultaneous expression of transcripts for a membrane-bound immunoglobulin and a secreted form of the same immunoglobulin in a single host cell.

Beerli, R., et al., (PNAS, vol. 105 (38), 14336-14341, 2008) describe a technology for the rapid isolation of fully human mAbs by isolation of antigen-specific B cells from human peripheral blood mononuclear cells (PBMC) and generation of recombinant, antigen-specific single-chain Fv (scFv) libraries which are screened by mammalian cell surface display using a Sindbis virus expression system, which is followed by isolation of fully human high-affinity antibodies following a single round of selection. Another display system used to screen, select and characterize antibody fragments based on display of full-length functional antibodies on the surface of mammalian cells relies on recombinase-mediated DNA integration coupled with high throughput FACS screening for selection of antibodies with very high antigen binding affinities is disclosed by Zhou et al. (mAbs 2:5, 508-518; 2010).

Mammalian cell based immunoglobulin libraries that rely on use of "removable-tether display vectors," or "transmembrane display vectors," which can be used for the expression of cell surface-bound immunoglobulins for affinity-based screening and the expression of secreted immunoglobulin are disclosed by Akamatsu et al., U.S. Pat. No. 8,163,546. In these "removable-tether display vectors", the polynucleotide encoding the cell surface tether domain is flanked by a first and a second restriction endonuclease site.

The invention disclosed herein provides improved libraries and screening methods for selecting a POI with desired characteristics.

Figure 8B:
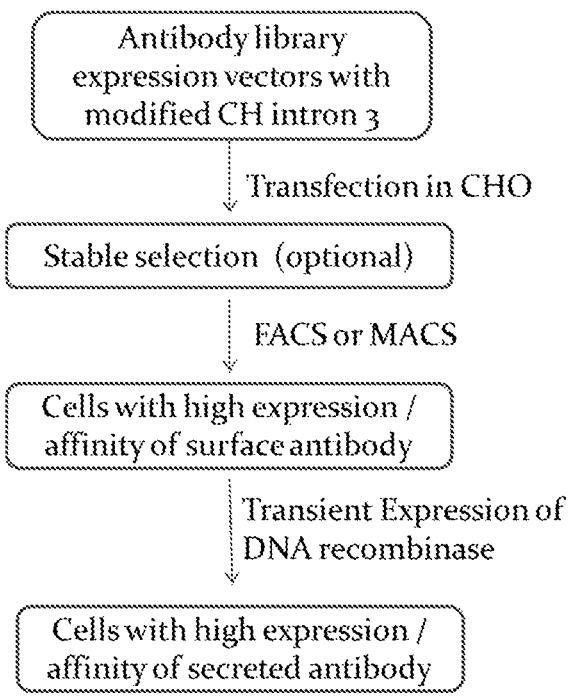

FIG. 8B illustrates an exemplary antibody library screening process utilizing alternative splicing and the switching mechanism. In one exemplary approach, a library of VH sequences can be cloned into an expression vector with modified Intron 3 as shown in FIG. 5C or 5D. A library of light chain sequences may be cloned into the same expression vector or into a separate vector. Expression of the antibody library vectors will result in an expression library of membrane-anchored antibodies. After transfection into CHO cells or other expression host cells, cells expressing antigen binding antibodies may be sorted or selected by FACS or MACS. Multiple rounds of sorting or selection may be performed under different stringent conditions to isolate production cells for antibodies with the best affinity for the antigen. The antibody sequences can be obtained from the selected cells by PCR or RT-PCR. The selected cells may be turned into production cells by expression of an appropriate site specific DNA recombinase to delete the MAD sequence. Similar designs may be applied to any engineered libraries of antibody or any other proteins. See, Example 8.

EXAMPLES

Example 1

Figure 9A:
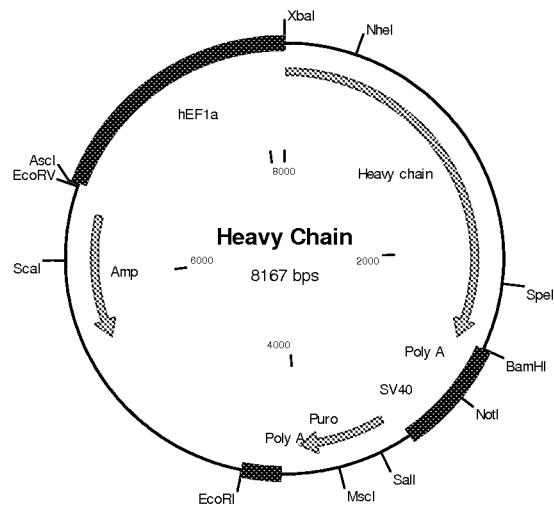
FIGS. 9A-C are plasmid maps of an antibody heavy chain expression vector (9A), an antibody light chain expression vector (9B) and an antibody heavy and light chain expression vector (9C).

Expression of Rituxan from Expression Vector Containing a LoxP Site in the $3^{rd}$ Intron of the Heavy Chain Genomic Sequence The Rituxan heavy chain variable sequence (VH) was gene synthesized and cloned into a mammalian expression vector containing the human IgG1 heavy chain constant region genomic sequence between restriction sites Xba I and Nhe I, to make vector LB0-H. The Rituxan VH sequence including signal peptide is shown in SEQ ID NO: 9. Expression of the antibody heavy chain was under the control of an EF1α promoter. The vector carries a Puromycin resistance gene for stable cell selection and an Ampicillin resistance gene for *E. coli* propagation. The plasmid map is shown in FIG. 9A.

Figure 9B:
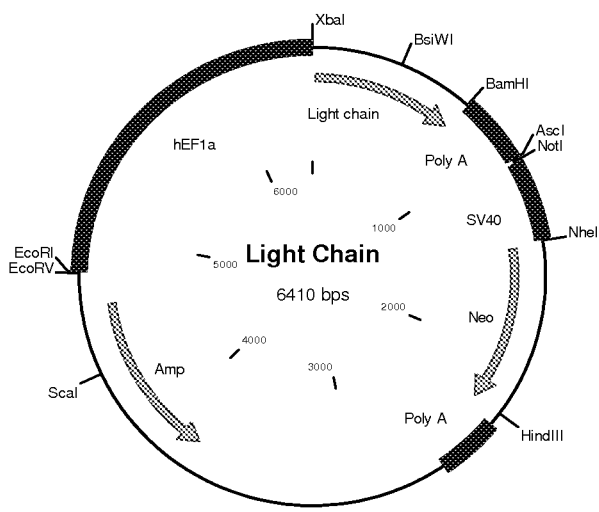

The Rituxan light chain cDNA was gene synthesized and cloned into a separate mammalian expression vector between restriction sites Xba I and BamH I to make vector LB0-K. The sequence of the light chain is shown in SEQ ID NO: 11. Expression of the antibody light chain was under the control of an EF1α promoter. It carries a Neomycin resistance gene for stable cell selection and an Ampicillin resistance gene for *E. coli* propagation. The plasmid map is shown in FIG. 9B.

A LoxP site was inserted into the middle of the $3^{rd}$ intron of Rituxan gamma genomic sequence in LB0-H by Bridge PCR to make vector LB1. The sequence of the heavy chain constant region is shown in SEQ ID NO: 13.

To express Rituxan, 293F cells (Invitrogen Inc.) were co-transfected with LB0-H or LB1, together with LB0-K. Transfection conditions were optimized with Freestyle Max transfection reagent (Invitrogen) and a GFP expression vector. 30 µg of DNA and 37.5 µl of Freestyle Max were used to transfect 30 ml of cells ($1\times10^6$ cells/ml). The cells were typically diluted 3 times the next day and subjected to flow cytometric analysis for GFP expression after one more day of culturing. Transfection efficiencies were determined to be ~80% for 293F cells under these conditions. To assess Rituxan expression, antibody levels in media were determined by dilution ELISA in which Rituxan was captured with goat anti-human IgG Fc (100 ng/well, Bethyl) and detected with the goat anti-human Kappa antibody HRP conjugates (1:10,000 dilution, Bethyl).

Figure 10A:
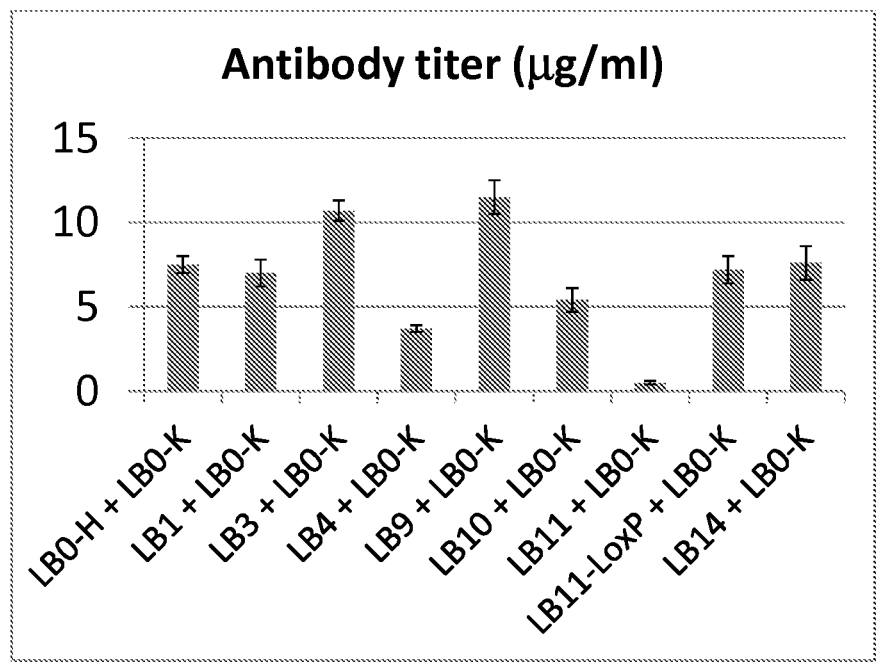
FIG. 10A shows Rituxan levels in culture media 2 days after transfection of 293F cells with Rituxan expression vectors.

Human IgG antibody (2 µg/ml of IgG, Sigma) was used as the standard for IgG quantitation. The expression levels are shown in FIG. 10A. LB1-transfected cells produced a similar amount of antibody as the wild-type control LB0-H, suggesting that the LoxP sequence inserted in the middle of the intron between CH2 and CH3 did not affect antibody expression levels. The heavy chain constant regions in both transfected cells were amplified by RT-PCR and sequenced. The RNA splicing was found to be identical with or without a LoxP site inside of the gamma chain intron.

Example 2

Expression of Rituxan Anchored on Cell Surface

Figure 9C:
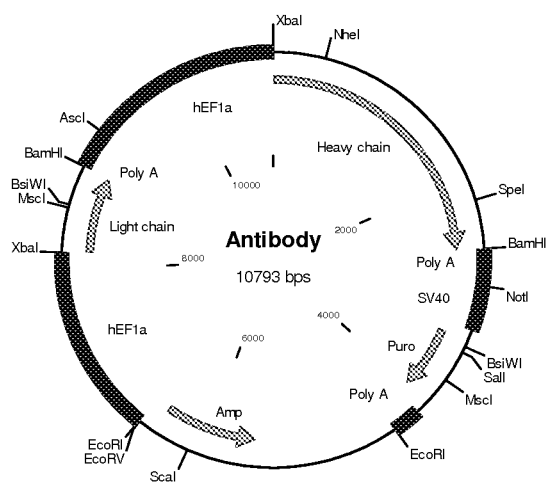

The human IgG1 CH3 sequence fused with the DAF GPI anchor signal sequence (SEQ ID NO: 4) or the PDGFR TM domain sequence (SEQ ID NO: 6) followed by LoxP and intron 3 sequences were synthesized and inserted into the $3^{rd}$ intron in LB1 to make vector LB3 or LB4, respectively, as shown in FIG. 5C. The sequences of the heavy chain constant region of LB3 and LB4 are shown in SEQ ID NO: 14 and SEQ ID NO: 15, respectively. The light chain expression cassette in LB0-K was digested with restriction enzymes EcoR V and Asc I. The DNA fragment of 2625 bp was then cloned into LB4 between EcoR V and Asc I to make Rituxan expression vector LB37. The plasmid map is shown in FIG. 9C. To assess Rituxan expression, 293F cells were co-transfected with heavy chain vectors LB3, or LB4, together with the light chain vector LB0-K using Freestyle Max transfection reagent.

The antibody titers in media were determined by dilution ELISA in which Rituxan was captured with goat anti-human IgG Fc (100 ng/well, Bethyl) and detected with the goat anti-human Kappa antibody HRP conjugates (1:10,000 dilution, Bethyl). Human IgG antibody (2 µg/ml of IgG, Sigma) was used as the standard for IgG quantitation. The expression levels are shown in FIG. 10A. Vectors employing the modified intron demonstrate robust expression of Rituxan ranging from 4-10 µg/ml in culture media after 2 days when cell densities are typically about $1\times10^6$ cells/ml. LB1-transfected cells produced a similar amount of antibody as the wild-type control LB0-H, suggesting that the LoxP sequence inserted in the middle of the intron between CH2 and CH3 did not affect antibody expression levels. LB3 secreted 2-3 times more antibody into the media than LB4, consistent with the fact that GPI-linked membrane anchorage is not 100%. This result has been reproduced in 3 independent experiments.

Figure 10B:
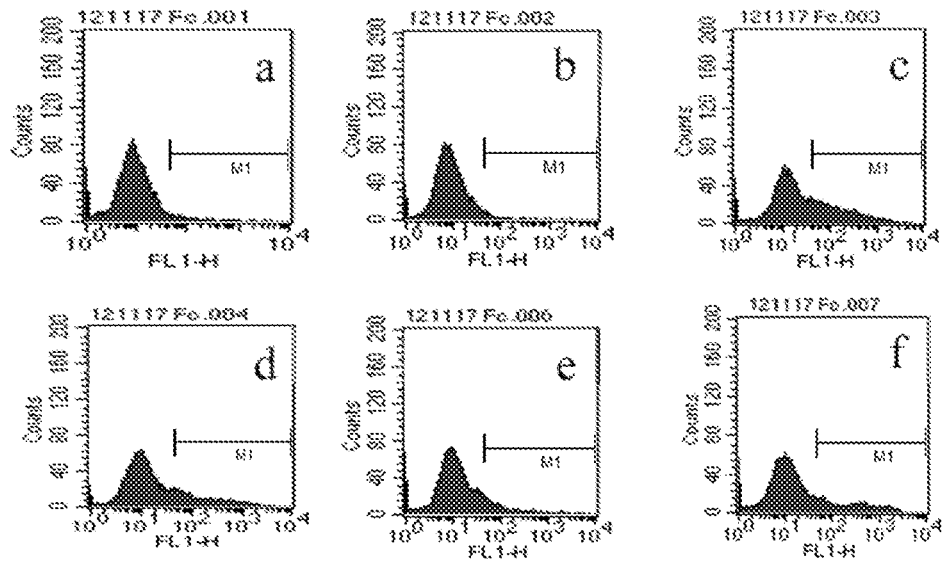
FIG. 10B shows FACS plots indicating cell surface Rituxan expression 2 days after transfection of 293F cells with Rituxan expression vectors.

The transfected 293F cells were also labeled with goat anti-human Fc antibody FITC conjugate (1:1,000 dilution, Bethyl) and subjected to flow cytometric analysis. 293F cells transfected with the wild-type CH3 exon vector (LB0-H, FIG. 10B.a) or LoxP modified CH3 exon vector (LB1, FIG. 10B.b) did not show cell surface antibody expression, whereas 293F cells transfected with alternatively spliced CH3-GASS vector (LB3, FIG. 10B.c) or CH3-TM vector (LB4, FIG. 10B.d) exhibited cell surface antibodies in 20-30% of the cells (Table 1).

TABLE 1

| Cell Surface Antibody Expression for Cells Transfected with Various Constructs. ||
|---|---|
| Transfection | MI % |
| LB0-H + LB0-K | 1.8 |
| LB1 + LB0-K | 1.1 |
| LB3 + LB0-K | 27.9 |
| LB4 + LB0-K | 20.1 |
| LB9 + LB0-K | 8.3 |
| LB10 + LB0-K | 16.5 |

Example 3

Expression of CH3 Deleted Rituxan Anchored on Cell Surface

The DAF GPI anchor signal sequence or the PDGFR TM domain sequence followed by LoxP and intron3 sequences were synthesized and inserted into the 3$^{rd}$ intron in LB1 to make vector LB9 or LB10, respectively, as shown in Figure D The sequences of the heavy chain constant region of LB9 and LB10 are shown in SEQ ID NO: 16 and SEQ ID NO: 17, respectively.

293F cells were co-transfected with LB9 or LB10, together with LB0-K using Freestyle Max transfection reagent. After 2 days the antibody levels in the media were assayed by ELISA similarly as described in Example 1. LB9-transfected cells secreted more antibodies into media than LB10-transfected cells (FIG. 10A), consistent with the result described in Example 2. The transfected 293F cells were also labeled with goat anti-human Fc antibody FITC conjugate (1:1,000 dilution, Bethyl) and subjected to flow cytometric analysis. 293F cells transfected with alternatively spliced vectors LB3 (FIG. 10B.e) or LB4 (FIG. 10B.f) exhibited cell surface expression of antibody in 8-20% of the cells (Table 1).

Example 4

Expression of Membrane-anchored GFP Upstream of the Rituxan Heavy Chain

Figure 1B:
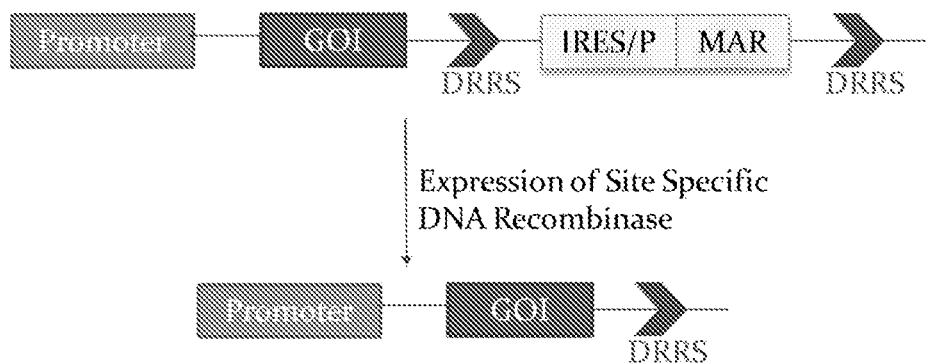
Figure 1C:
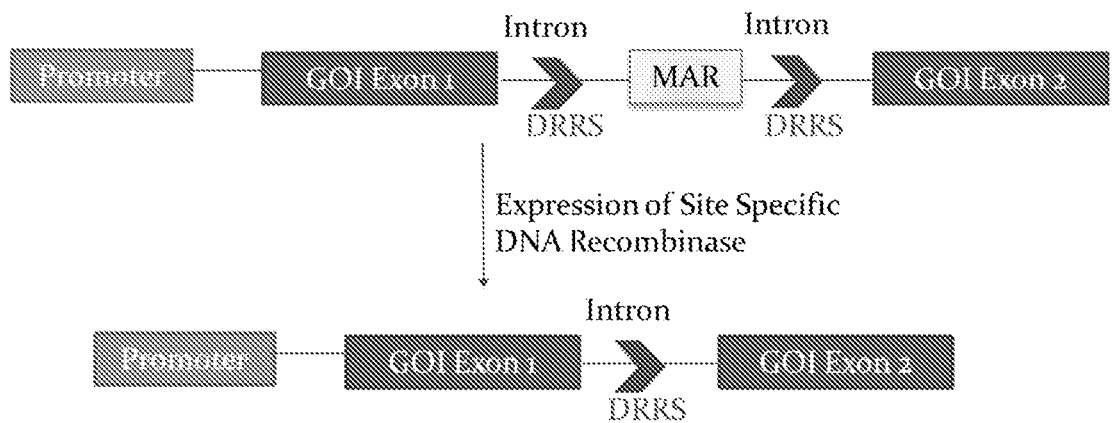

The membrane-anchored GFP (SEQ ID NO: 1) carrying a Kosak consensus sequence was flanked by two LoxP sites, and inserted between the EF1α promoter and the Rituxan gamma sequence in the vector LB0-H to make vector LB11, as described in FIG. 1A. The sequence between the 2 LoxP sites was deleted in LB11 and only one LoxP site remained to make vector LB11-LoxP. 293F cells were co-transfected with LB0-H, LB11, or LB11-LoxP, together with LB0-K using Freestyle Max transfection reagent. After 2 days, antibody levels were assayed by ELISA as described in Example 1. LB11-transfected cells produced less than 10% of relative to LB0-H-transfected cells (FIG. 10A), suggesting that the presence of the GFP cassette upstream of the Rituxan heavy chain gene greatly diminished expression of Rituxan. After removal of the GFP cassette, LB11-LoxP produced Rituxan at a similar level to LB0-H (FIG. 10A). Expression of GFP in LB11-transfected cells was confirmed by flow cytometric analysis.

Example 5

Expression of Membrane-anchored GFP Downstream of the Rituxan Heavy Chain

An IRES sequence (SEQ ID NO: 18) was fused with the membrane-anchored GFP (SEQ ID NO: 1) carrying a Kosak consensus sequence. A LoxP site was then added at both N- and C-terminals. The whole sequence was inserted downstream of the Rituxan gamma stop codon and before the poly A signal in the vector LB0-H to make vector LB14, as described in FIG. 1B. 293F cells were co-transfected with LB14 and LB0-K using Freestyle Max transfection reagent. After 2 days, the antibody level in the media was assayed by ELISA as described in Example 1, and was shown in FIG. 10A. Expression of GFP in LB11-transfected cells was confirmed by flow cytometric analysis.

Example 6

Switching Off the Membrane-anchored Antibody by Providing Cre

A Cre expression vector LB30 was constructed. The Cre cDNA was human codon optimized and fused with a peptide of MPKKKRK (SEQ ID NO: 19) at the N-terminus for nuclear localization. Expression of Cre was driven by a human EF1α promoter.

Figure 11A:
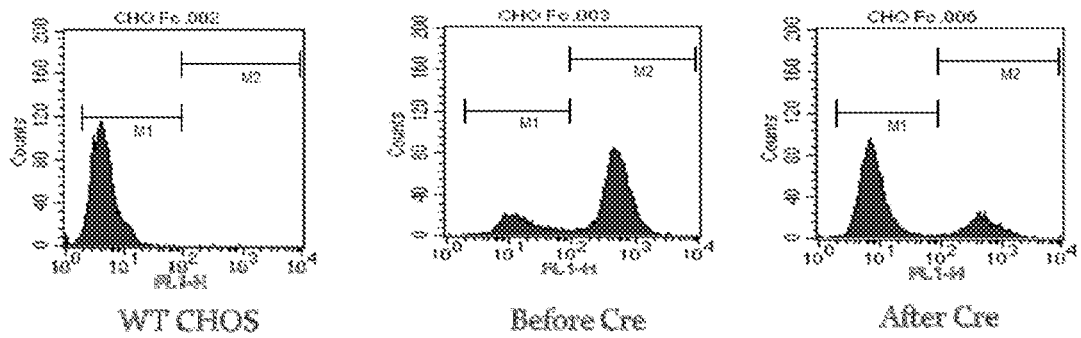
FIG. 11A shows that membrane-anchored antibody expression was switched off by transient transfection of a Cre expression vector ("After Cre").

The 293F cells were transfected with LB37 linearized with restriction enzyme Asc I using Freestyle Max transfection reagent, and cultured in the presence of 1 μg/ml of Puromycin and 400 μg/ml of G418. After selection for approximately 2 weeks, the stable pool was transiently transfected with the Cre expression vector LB30. After one more week of culture, the cells were labeled with goat anti-human Fc antibody FITC conjugate (1:1,000 dilution, Bethyl) and subjected to flow cytometric analysis to assess cell surface Rituxan expression. Most of the cells lost membrane-anchored antibody after Cre transfection as shown in FIG. 11A ("After Cre").

Figure 11B:
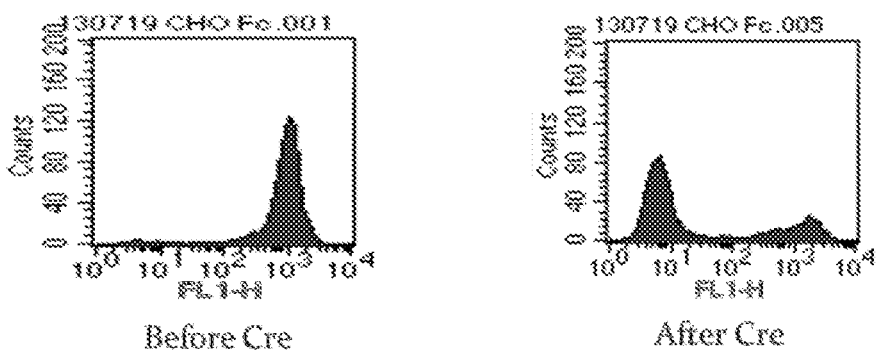
FIG. 11B shows that membrane-anchored antibody expression was switched off by treatment of cells with recombinant Cre ("After Cre").

Switching off the membrane-anchored antibody was also achieved by providing recombinant Cre in the cell culture. A cell line expressing membrane-anchored antibody cloned from the stable pool described above was treated with 1 μM of recombinant Cre fused with TAT-NLS for nuclear localization (Excellgen, Inc.) for 2 hours. After one additional week of culture, the cells were assessed for cell surface antibody expression, as described above. Most of the cells lost membrane-anchored antibody as shown in FIG. 11B ("After Cre").

Example 7

Screening of Highly Productive Humira Production Cell Lines

The variable sequence of Humira light chain (SEQ ID NO: 20) was gene synthesized and cloned into LB0-K between restriction sites Xba I and BsiW I to make vector LB42. The variable sequence of Humira heavy chain (SEQ ID NO: 22) was gene synthesized and cloned into LB4 between restriction sites XbaI and Nhe I to make vector LB25. The light chain expression cassette in LB42 was digested with restriction enzymes EcoR V and Asc I. the DNA fragment of 2641 bp was then cloned into LB25 between EcoR V and Asc I to make Humira expression vector LB29.

Figure 12A:
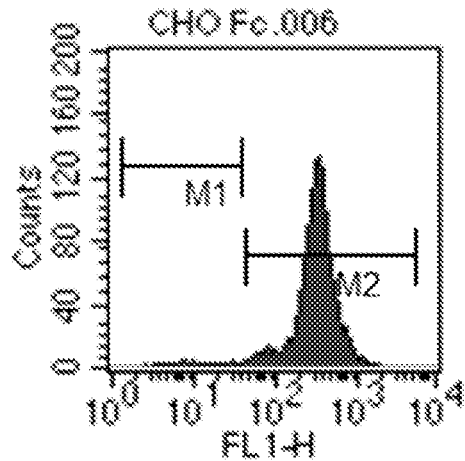
FIG. 12A shows that cell surface antibody of a CHOS cell line that expresses both membrane-anchored Humira and secreted Humira via alternative splicing.
Figure 12B:
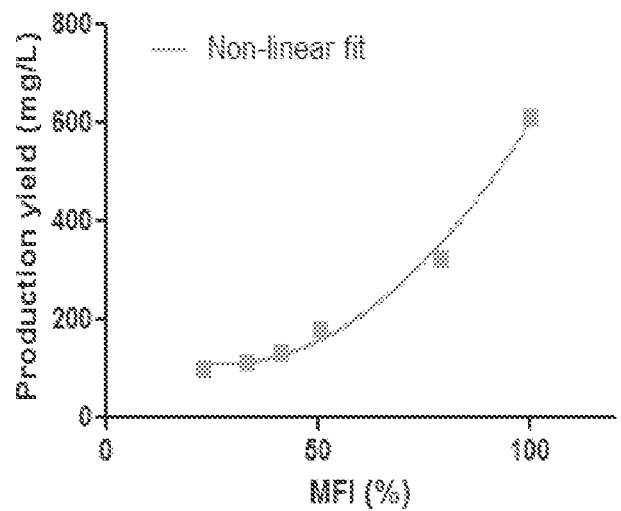
FIG. 12B shows that the membrane antibody expression correlates strongly with the secreted antibody levels in cells that express both membrane-anchored Humira and secreted Humira via alternative splicing.
Figure 13:
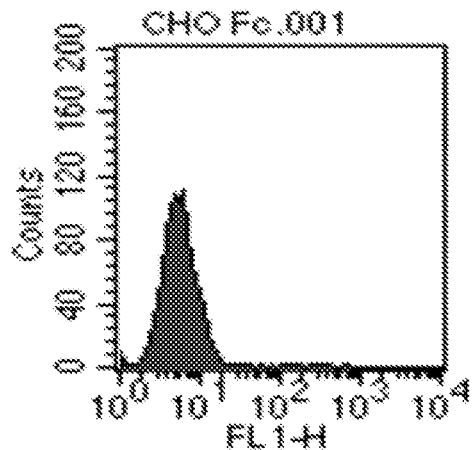
FIG. 13 shows lack of surface antibody on a Humira expressing cell line after switching off membrane anchorage.

CHOS cells (Invitrogen, Inc.) were cultured in Freestyle CHO media (Invitrogen, Inc.). 1×10$^8$ CHOS cells were transfected with LB29 linearized with restriction enzyme Asc I using Freestyle Max transfection reagent, and then selected with 10 ug/ml of Puromycin for 2 weeks. 1×10$^7$ stable cells were labeled with goat anti-human Fc antibody FITC conjugate (1:1,000 dilution, Bethyl) and subjected to FACS sorting. The 0.01% of the cells with the highest expression of cell surface antibodies were sorted into five 96-well plates. Approximately 100 colonies grew out after 2-3 weeks. The culture media was screened for expression of Humira by ELISA as described in Example 1. The 24 highest expressing clones were picked, expanded, and cryopreserved. Six clones with different levels of antibody expression were picked for cell surface antibody assessment. They were labeled with goat anti-human Fc antibody FITC conjugate (1:1,000 dilution, Bethyl) and subjected to flow cytomeric analysis to confirm membrane-anchored antibody expression (FIG. 12A). They were also subjected to 30 ml of shaking culture. The antibody production in the culture media was assessed by ELISA as described in Example 1 after 7-day non-fed batch culture. Higher membrane antibody expression was found to be strongly correlated with increased, secreted antibody production (FIG. 12B). The 0.01% of stable cells transfected with linearized LB29 having the highest expression of cell surface antibodies was also sorted into a pool. After culturing for a week, the selected pool was transiently transfected with the Cre expression vector described in Example 6 with Neon Transfection System (Invitrogen, Inc.). After one more week of culturing, the cells were cloned into ten 96-well plates by limiting dilution. Approximately 200 colonies grew out after 2-3 weeks. The culture media was screened for expression of Humira by ELISA as described in Example 1. The 24 clones having the highest level of antibody in the media were picked and expanded to a 24-well plate. After 3 days of culturing, the culture media was screened again for expression of Humira. The 12 clones having the highest level of antibody in the media were picked, expanded, and cryopreserved. The cells were confirmed to lack of membrane-anchored antibody (FIG. 13A). The antibody production in culture media was assessed after 7-day non-fed batch culture in a 30 ml of shaking culture. Antibody yields of the 5 clones having the highest level of antibody in the media are shown in Table 2.

TABLE 2

Humira Antibody Production In Culture Media.

| Clone | Peak cell density (cells/ml) | Yield (mg/L) |
|---|---|---|
| 61.7B11 | $4.1 \times 10^6$ | 282 |
| 61.13C9 | $4.8 \times 10^6$ | 320 |
| 61.14E8 | $4.9 \times 10^6$ | 154 |
| 61.14F6 | $5.3 \times 10^6$ | 390 |
| 61.15G6 | $5.2 \times 10^6$ | 752 |

Example 8

A Model Screening of Antibody Library

Figure 14:
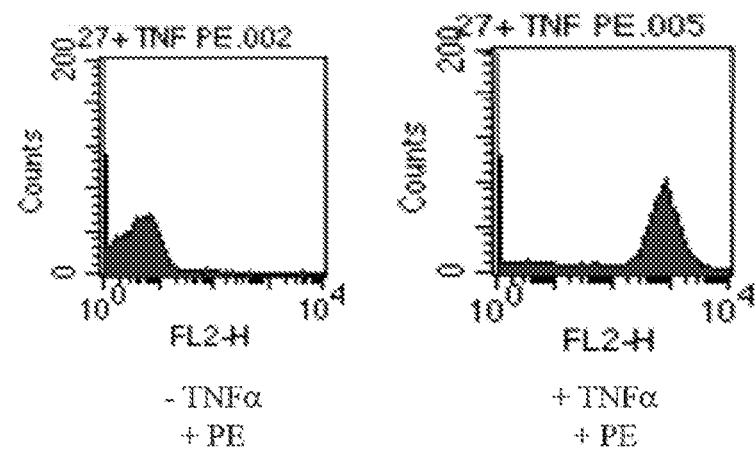
FIG. 14 shows that a CHOS cell line expressing membrane-anchored Humira stained positively after binding with biotinylated TNFα and streptavidin Phycoerythrin conjugates.

One cell line selected in Example 7 and designated #27 expresses membrane-anchored Humira. Cells from cell line #27 were treated with 1 µg/ml of biotinylated human TNFα (ACRO Biosystems, Inc.) for 30 min. After washing once with PBS, the cells were labeled with streptavidin Phycoerythrin conjugate (VectorLabs, Inc.) for 30 min. After washing twice with PBS, the cells were subjected to flow cytometric analysis and exhibited positive binding of TNFα on cell surface Humira (FIG. 14). The cell line #27 was spiked at a ratio of 1:1000 into a stable pool of CHOS cells transfected with Rituxan expression vector LB37. After binding with biotinylated TNFα and then streptavidin Phycoerythrin conjugates, the cells were subjected to FACS sorting. 1000 positive cells were sorted into a pool. After culturing for 2 weeks, the antibody sequence in the FACS positive cells was amplified by RT-PCR and confirmed to be the Humira antibody sequence.

What is claimed is:

1. A cell line screening method comprising,
(a) providing a plurality of host cells transfected with a plurality of DNA constructs, wherein each host cell integrates the DNA construct to make a library of constructs in the plurality of host cells, and wherein the DNA constructs comprise a nucleic acid encoding a protein of interest, a nucleic acid encoding a reporter, a first DNA recombinase recognition sequence and a second DNA recombinase recognition sequence, wherein the first DNA recombinase recognition sequence is located upstream of the nucleic acid encoding the reporter and the second DNA recombinase recognition sequence is located downstream of the nucleic acid encoding the reporter whereby a DNA recombinase is capable of removing the nucleic acid encoding the reporter leaving the gene of interest intact, wherein the nucleic acid encoding the protein of interest is operably linked to a promoter, and wherein the nucleic acid encoding the reporter is also operably linked to the promoter;

(b) culturing the transfected cells in a cell culture media wherein the reporter is expressed;

(c) screening the transfected host cells for the reporter, and selecting the host cells that express more of the reporter than most of the other host cells whereby the host cells expressing a more of the protein of interest than most of the host cells are also selected;

(d) exposing the selected host cells to the DNA recombinase wherein the DNA recombinase acts at the DNA recombinase recognition sequences whereby the cells no longer express the reporter and the cells continue to express the protein of interest; and (e) confirming the cells express a desired amount of the protein of interest.

2. The method of claim 1, wherein the DNA recombinase recognition sequence and the DNA recombinase are selected from the group consisting of a DNA recombinase recognition sequence for a FLP recombinase and a FLP recombinase, a DNA recombinase recognition sequence for a Cre recombinase and a Cre recombinase, and a DNA recombinase recognition sequence for a φC31 integrase and a φC31 integrase.

3. The method of claim 1, wherein the nucleic acid encoding the reporter is downstream of the nucleic acid encoding the protein of interest.

4. The method of claim 1, wherein the DNA constructs further comprise an IRES upstream of the nucleic acid encoding the reporter.

5. The method of claim 1, wherein the reporter can be detected by a fluorescence-activated cell sorting.

6. The method of claim 5, wherein the reporter in the transfected host cells is screened using the fluorescence-activated cell sorting.

7. The method of claim 1, wherein the protein of interest is secreted into the cell culture media.

8. The method of claim 1, wherein the protein of interest is an antibody polypeptide.

9. The method of claim 8, wherein the protein of interest is secreted into the cell culture media.

10. The method of claim 1, wherein the plurality of DNA constructs encode a plurality of different proteins of interest.

11. The method of claim 10, wherein the plurality of DNA constructs encode an antibody library.

12. The method of claim 11, wherein the antibody library is an affinity maturation library.

13. The method of claim 11, wherein the promoter is an endogenous promoter.

14. The method of claim 11, wherein the promoter is a heterologous promoter.

15. A cell line screening method comprising, (a) providing a plurality of host cells transfected with a plurality of DNA constructs, wherein each host cell integrates the DNA construct to make a library of constructs in the plurality of host cells, and wherein the DNA constructs comprise a nucleic acid encoding a protein of interest, a nucleic acid encoding a reporter, a first LoxP or a first LoxP variant sequence and a second LoxP sequence or a second LoxP variant sequence, wherein the first LoxP sequence or first LoxP variant sequence is located upstream of the nucleic acid encoding the reporter and the second LoxP sequence or LoxP variant sequence is located downstream of the nucleic acid encoding the reporter whereby a Cre recombinase is capable of removing the nucleic acid encoding the reporter leaving the gene of interest intact, wherein the nucleic acid encoding the protein of interest is operably linked to a promoter, and wherein the nucleic acid encoding the reporter is also operably linked to the promoter;

(b) culturing the transfected cells in a cell culture media wherein the reporter is expressed;

(c) screening the transfected host cells for the reporter, and selecting the host cells that express more of the reporter than most of the other host cells whereby the host cells expressing more of the protein of interest than the other host cells are also selected;

(d) exposing the selected host cells to the Cre recombinase wherein the Cre recombinase acts at the LoxP sequence or the LoxP variant sequence whereby the cells no longer express the reporter and the cells continue to express the protein of interest; and (e) confirming the cells express a desired amount of the protein of interest.

16. The method of claim 15, wherein the nucleic acid encoding the reporter is downstream of the nucleic acid encoding the protein of interest.

17. The method of claim 15, wherein the reporter can be detected by a fluorescence-activated cell sorting.

18. The method of claim 17, wherein the reporter in the transfected host cells is screened using the fluorescence-activated cell sorting.

19. The method of claim 15, wherein the protein of interest is secreted into the cell culture media.

20. The method of claim 15, wherein the protein of interest is an antibody polypeptide.

* * * * *